(12) United States Patent
Jones et al.

(10) Patent No.: US 7,265,129 B2
(45) Date of Patent: Sep. 4, 2007

(54) ANTI-INFECTIVE BIARYL COMPOUNDS

(75) Inventors: Peter Jones, Bridgnorth (GB); Roland W. Burli, San Francisco, CA (US); Chun Jiang, Los Altos, CA (US); Dustin L. McMinn, Pacifica, CA (US)

(73) Assignee: Genesoft Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 10/532,271

(22) PCT Filed: Oct. 24, 2003

(86) PCT No.: PCT/US03/33617

§ 371 (c)(1),
(2), (4) Date: Nov. 8, 2005

(87) PCT Pub. No.: WO2004/039318

PCT Pub. Date: May 13, 2004

(65) Prior Publication Data

US 2006/0148845 A1    Jul. 6, 2006

Related U.S. Application Data

(60) Provisional application No. 60/421,438, filed on Oct. 25, 2002.

(51) Int. Cl.
C07D 471/02 (2006.01)
C07D 403/02 (2006.01)
A61K 31/4745 (2006.01)
A61K 31/42 (2006.01)

(52) U.S. Cl. ............... 514/303; 514/258; 514/307; 514/394; 544/256; 546/118; 546/144; 548/304.4

(58) Field of Classification Search ............ 546/118, 546/144; 544/256; 548/304.4; 514/258, 514/303, 307, 394
See application file for complete search history.

(56) References Cited

U.S. PATENT DOCUMENTS

| | | | |
|---|---|---|---|
| 3,622,574 A | 11/1971 | Wright et al. | |
| 4,738,980 A | 4/1988 | Arcamone et al. | |
| 4,766,142 A | 8/1988 | Arcamone et al. | |
| 4,800,211 A | 1/1989 | Tischler et al. | |
| 4,912,199 A | 3/1990 | Lown et al. | |
| 5,017,599 A | 5/1991 | Lazzari et al. | |
| 5,049,579 A | 9/1991 | Lazzari et al. | |
| 5,310,752 A | 5/1994 | Lazzari et al. | |
| 5,350,748 A | 9/1994 | Boschelli et al. | |
| 5,395,849 A | 3/1995 | Wittman et al. | |
| 5,472,976 A | 12/1995 | Animati et al. | |
| 5,502,068 A | 3/1996 | Lown et al. | |
| 5,545,640 A | 8/1996 | Beaulieu et al. | |
| 5,616,606 A | 4/1997 | Lown et al. | |
| 5,670,534 A | 9/1997 | Animati et al. | |
| 5,698,674 A | 12/1997 | Bruice et al. | |
| 5,753,629 A | 5/1998 | Beria et al. |
| 5,801,155 A | 9/1998 | Kutyavin et al. |
| 5,808,087 A | 9/1998 | Matsunaga et al. |
| 5,821,258 A | 10/1998 | Matsunaga |
| 5,844,110 A | 12/1998 | Gold |
| 5,852,011 A | 12/1998 | Matsunaga et al. |
| 5,998,140 A | 12/1999 | Dervan et al. |
| 6,090,947 A | 7/2000 | Dervan et al. |
| 6,143,901 A | 11/2000 | Dervan |
| 6,153,642 A | 11/2000 | Cozzi et al. |
| 6,172,104 B1 | 1/2001 | Tidwell et al. |
| 6,458,768 B1 | 10/2002 | Cozzi et al. |
| 6,555,693 B2 | 4/2003 | Ge et al. |
| 6,566,393 B1 | 5/2003 | Lee et al. |

(Continued)

FOREIGN PATENT DOCUMENTS

| DE | 199 20 936 A1 | 11/2000 |
|---|---|---|
| GB | 2 310 207 A | 2/1996 |
| JP | 08-027146 A | 10/1996 |
| JP | 08-269008 A | 10/1996 |
| JP | 11-171886 A | 6/1999 |
| JP | 11-189594 A | 7/1999 |
| WO | WO92/13838 A1 | 8/1992 |
| WO | WO93/13739 A2 | 7/1993 |
| WO | WO94/20463 A1 | 9/1994 |
| WO | WO95/24419 A1 | 9/1995 |
| WO | WO96/26950 A1 | 9/1996 |
| WO | WO97/03957 A1 | 2/1997 |
| WO | WO97/25351 A2 | 7/1997 |
| WO | WO97/28123 A1 | 8/1997 |
| WO | WO98/21202 A1 | 5/1998 |
| WO | WO98/35702 A1 | 8/1998 |

(Continued)

OTHER PUBLICATIONS

Arcamone, F. et al., "Synthesis, DNA binding and antiviral activity of distamycin analogues containing different heterocyclic moieties." *Anti-Cancer Drug Design*, 1:235-244 (1986).

(Continued)

*Primary Examiner*—Zinna N. Davis
(74) *Attorney, Agent, or Firm*—Townsend and Townsend and Crew LLP

(57) ABSTRACT

Compounds represented by the formula (I), where R1, R2, R3, R4, R5, and Q are as defined herein, exhibit activity against infectious pathogens

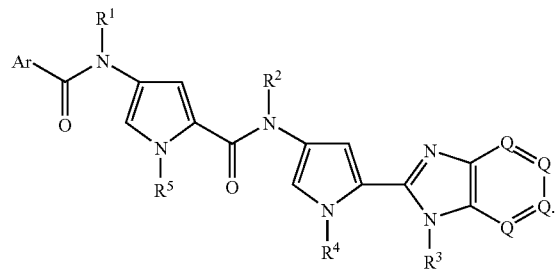

24 Claims, 18 Drawing Sheets

U.S. PATENT DOCUMENTS

| | | |
|---|---|---|
| 6,586,561 B1 | 7/2003 | Litt et al. |
| 6,716,866 B2 | 4/2004 | McMinn et al. |
| 6,777,425 B2 | 8/2004 | Bürli et al. |
| 6,825,228 B2 | 11/2004 | Bürli et al. |
| 2003/0199516 A1 | 10/2003 | Moser et al. |
| 2003/0211508 A1 | 11/2003 | Ge et al. |
| 2003/0236198 A1 | 12/2003 | Bürli et al. |
| 2005/0004042 A1 | 1/2005 | Hu et al. |

FOREIGN PATENT DOCUMENTS

| | | |
|---|---|---|
| WO | WO98/37066 A1 | 8/1998 |
| WO | WO98/37067 A1 | 8/1998 |
| WO | WO98/37087 A1 | 8/1998 |
| WO | WO98/43663 A1 | 10/1998 |
| WO | WO98/45284 A1 | 10/1998 |
| WO | WO98/49142 A1 | 11/1998 |
| WO | WO98/50582 A1 | 11/1998 |
| WO | WO98/52614 A2 | 11/1998 |
| WO | WO99/00364 A1 | 1/1999 |
| WO | WO99/25686 A1 | 5/1999 |
| WO | WO99/27939 A1 | 6/1999 |
| WO | WO99/41367 A1 | 8/1999 |
| WO | WO99/50265 A1 | 10/1999 |
| WO | WO99/50266 A1 | 10/1999 |
| WO | WO99/62890 A1 | 12/1999 |
| WO | WO99/64413 A1 | 12/1999 |
| WO | WO 00/06541 A1 | 2/2000 |
| WO | WO 00/06542 A1 | 2/2000 |
| WO | WO 00/15209 A2 | 3/2000 |
| WO | WO 00/15773 A2 | 3/2000 |
| WO | WO 00/40605 A2 | 7/2000 |
| WO | WO 00/69432 A1 | 11/2000 |
| WO | WO 01/10439 A1 | 2/2001 |
| WO | WO 01/19792 A1 | 3/2001 |
| WO | WO 01/21615 A1 | 3/2001 |
| WO | WO 01/74898 A2 | 10/2001 |
| WO | WO 01/96313 A1 | 12/2001 |
| WO | WO 02/00650 A2 | 1/2002 |
| WO | WO 02/088119 A1 | 11/2002 |
| WO | WO 02/101073 A2 | 12/2002 |
| WO | WO 2004/012736 A1 | 2/2004 |

OTHER PUBLICATIONS

Bailly, C. and J.B. Chaires, "Sequence-specific DNA minor groove binders. Design and synthesis of netropsin and distamycin analogues." *Bioconj. Chem.*, 9(5):513-538 (1998).

Baird, E.E. and P.B. Dervan, "Solid phase synthesis of polyamides containing imidazole and pyrrole amino acids." *J. Am. Chem. Soc.*, 118:6141-46 (1996).

Baraldi et al., "Synthesis of 3-Substituted-7-alkoxy-5H-pyrazolo [4,3-d],2,3-triazin-4(3H)-ones" *Synthesis*, pp. 1437-1440, (1994), XP002208604.

Baraldi, P.G. et al., "Synthesis and antitumor activity of new benzoheterocyclic derivatives of distamycin A." *J. Med. Chem.*, 43:2675-2684 (2000).

Berge, S.M., et al, "Pharmaceutical Salts", *J. Pharm. Sci.*, 66:1-19 (1977).

Bilder G. et al., "Restenosis following angioplasty in the swine coronary artery is inhibited by an orally active PDGF-receptor tyrosine kinase inhibitor, RPR101511A." *Circulation*, 99(25):3292-99 (1999).

Boger, D.L. et al., "A simple, high-resolution method for establishing DNA binding affinity and sequence selectivity." *J. Am. Chem. Soc.*, 123:5878-91 (2001).

Boger, D.L. et al., "Total synthesis of distamycin A and 2640 analogues: A solution-phase combinatorial approach to the discovery of new bioactive DNA binding agents and development of a rapid high-throughput screen for determining relative DNA binding affinity or DNA binding sequence selectivity." *J. Am. Chem. Soc.*, 122:6382-94 (2000).

Bremer, R.E. et al., "Recognition of the DNA minor groove by pyrrole-imidazole polyamides: comparison of desmethyl-and n-methylpyroole." *Bioorg. Med. Chem.*, 8:1947-55 (2000).

Bruice, Thomas C. et al., "Rational design of substituted tripyrrole peptides that complex with DNA by both slelective minor-groove binding and electrostatic interaction with the phosphate backbone." *Proc. Natl. Acad. Sci. USA*, 89:1700-04 (1992).

Chiarino, D. et al., "Synthesis of new isoxazole aminoalcohols." *J. Heterocyclic Chem.*, 25(1):337-342 (1988).

Choudhury, G.G. et al., "Involvement of PKC-alpha in PDGF-mediated mitogenic signaling in human mesangial cells." *Am. J. Physiol.*, 265(5 Pt 2):F634-42 (1993).

Corallini, A. et al. "Characterization of the effects of two polysulfonated distamycin A derivatives, PNU145156E and PNU153429, on HIV type 1 Tat protein." *AIDS Res. Hum. Retroviruses*, 4(17):1561-71 (1998).

Dyatkina, N.B. et al., "Minor grove DNA binders as antimicrobial agents. 1. Pyrrole tetraamides are potent antibacterials against vancomycin resistant Enterococci [corrected] and methicillin resistant *Staphyloccus aureus*." *J. Med. Chem.*; 45(4):805-17 (2002).

Ellervik, U. et al., "Hydroxybenzamide/pyrrole pair distinguishes T·A from A·T base pairs in the minor groove of DNA" *J. Am. Chem. Soc.* 122(39):9354-60 (2000).

El-Naggar, A.M. et al., "Synthesis of some 2-thenoyl-, 5-bromo-2-thenoyl- and 5-nitro-2-thenoylamino acid derivatives and their antimicrobial activity." *J. Indian Chem. Soc.*, LIX:783-786 (1982).

Fenwick et al., "Solid-phase synthesis of cyclic alkoxyketones, inhibitors of the cysteine protease cathepsin K." *Bioorg. Med. Chem. Lett.*, 11:195-98 (2001).

Floreancig, P.E. et al., "Recognition of the minor groove of DNA by hairpin polyamides containing alpha-substituted-beta-amino acids." *J. Am. Chem. Soc.*, 122:6342-50 (2000).

Goodsell D. and R.E. Dickerson, "Isohelical analysis of DNA groove-binding drugs." *J. Med. Chem.*, 29(5):727-33 (1986).

Gougerot-Pocidalo, M.A. et al. "Mechanisms by which oxidative injury inhibits the proliferative response of human lymphocytes to PHA. Effect of the thiol compound 2-mercaptoethanol." *Immunology*; 64(2):281-8 (1988).

Gupta et al., "Hybrid molecules containing propargylic sulfones and DNA minor groove-binding lexitropsins: synthesis, sequence specificity of reaction with DNA and biological evaluation." *Gene*, 149:81-90 (1994).

Handler, J.A. et al., "Mitogenic signaling by epidermal growth factor (EGF), but not platelet-derived growth factor, requires arachidonic acid metabolism in BALB/c 3T3 cells. Modulation of EGF-dependent c-myc expression by prostaglandins." *J. Biol. Chem.*, 265(7):3669-73 (1990).

Heldin C.H. and B. Westermark, "Mechanism of action and in vivo role of platelet-derived growth factor." *Physiol. Rev.*; 79(4):1283-316 (1999).

Herman, D.M. et al., "Cycle Polyamide Motif for Recognition of the Minor Groove of DNA." *J. Am. Chem. Soc.*, 121(6):1121-29 (1999).

Kelly, J.J. et al., "Binding site size limit of the 2:1 pyrrole-imidazole polyamide-DNA motif." *Proc. Natl. Acad. Sci. USA*, 93:6981-85 (1996).

Khalaf, A.I. et al., "The synthesis of some head to head linked DNA minor groove binders." *Tetrahedron*, 56:5225-39 (2000).

Kopka, M.L. et al., "Defining GC-specificity in the minor groove: side-by-side binding of the di-imidazole lexitropsin to C-A-T-G-G-C-C-A-T-G." *Structure*, 5(8):1033-46 (1997).

Machon, Z. and S. Ryng, "Synthesis and biological properties of 5-benzoylamino-3-methyl-4-isoxazolocarboxylic acid derivatives." *Arch. Immunol. Ther. Exp. (Warsz).*, 29(6):813-21 (1981).

Matsuba, Y. et al., "A novel synthetic DNA minor groove binder, MS-247: antitumor activity and cytotoxic mechanism." *Cancer Chemo. Pharm.*, 46:1-9 (2000).

Matsumoto, T. et al., "Synthesis of sulfonamido oligo-*N*-methylpyrrole-carboxamide derivatives and their photochemical DNA cleaving activities." *Heterocycles*, 33(1):135-138 (1992).

Matusomoto, T. et al., "Synthesis of sulfonamido oligo-*N*-methylpyrrole-carboxamide derivatives and their photochemical DNA cleaving activities." *Heterocycles*, 34(9):1697-1702 (1992).

Mrksich, M. et al., "Hairpin peptide motif, a new class of oligopeptides for sequence-specific recognition in the minor groove of double-helical DNA." *J. Am. Chem. Soc.*, 116:7983-88 (1994).

Neidle, S., "DNA minor-groove recognition by small molecules." *Nat. Prod. Rep.*, 18:291-309 (2001).

Nguyen, J.T. et al. "Exploiting the basis of proline recognition by SH3 and WW domains: design of N-substituted inhibitors." *Science*, 282(5396):2088-92 (1998).

Nielsen, P.E. "Sequence-Selective DNA Recognition by Synthetic Ligands." *Bioconjug. Chem.*, 2(1):1-12 (1991).

Pae, A.N. et al., "Synthesis and in vitro activity of new oxazolidinone antibacterial agents having substituted isoxazoles", *Bioorg. Med. Chem. Lett.*, 9:2679-84 (1999).

Plescia, S. et al., "3α-hydroxysteroid dehydrogenase inhibitory activity of some N(3)-(1-R-4-carboxypyrazol-5-yl)-1,2,3,-benzotriazin-4(3H)-one and quinazoline-4(3H)-one acids." *Il Farmaco*, 49(7,8):505-07 (1994).

Plouvier, B. et al., "DNA-sequence specific recognition by a thiazole analogue of netropsin: a comparative footprinting study." *Nucl. Acids Res.*, 19(21):5821-5829 (1991).

Rao, K.E. et al., "Interaction of synthetic analogues of distamycin and netropsin with nucleic acids. Does curvature of ligand play a role in distamycin-DNA interactions?" *Biochemistry*, 27(8):3018-24 (1988).

Rao, K.E. et al., "Molecular recognition between oligopeptides and nucleic acids: DNA sequence specificity and binding properties of thiazole-lexitropsins incorporating the concepts of base site acceptance and avoidance." *Anti-Cancer Drug Design*, 5:3-20 (1990).

Renkema, G.H. and K. Saksela, "Interactions of HIV-1 NEF with cellular signal transducing proteins." *Frontiers in Bioscience*, 5:d268-83 (2000).

Sakai, Y. et al., "Synthesis of halogenated thiazole derivatives of oligo-N-methylpyrrolecarboxamide and their photochemical DNA cleaving activities." *Heterocycles*, 36(3):565-73 (1993).

Sen et al., "Synthesis of Compounds Related to Reserpine Skeleton." *J. Indian Chem. Soc.*, 46(3):209-15, also in *Chemical Abstracts* 71(1):318 (1969).

Sharma et al., "Design and Synthesis of Novel Thiazole-Cantaining Cross-Linked Polyamides Related to the Antiviral Antibiotic Distamycin." *J. Org. Chem*, p. est: 5.3 (1999).

Tanis, Steven P. and David B. Head, "Furans in synthesis. The preparation of (.+−.)- lactaral", *Tetrahedron Lett.*, 23:(52) pp. 5509-5512 (1982).

Taylor, J.S. et al., "DNA affinity cleaving : Sequence specific cleavage of DNA by Distamycin-EDTA—Fe(II) and EDTA-distamycin Fe(II)." *Tetrahedron*, 40(3):457-65 (1984).

Trauger, J.W. et al., "Recognition of DNA by designed ligands at subnanomolar concentrations." *Nature*, 382:559-61 (1996).

Vaquero et al., "Small ligands that neither bing to nor alter the structure of d(GA.TC)n sequences in DNA." *FEBS Letters*, 420:156-60 (1997).

Wade W.S. et al., "Binding affinities of synthetic peptides, pyridine-2-carboxamidonetropsin and 1-methylimidazole-2-carboxamidonetropsin, that form 2:1 complexes in the minor groove of double-helical DNA." *Biochemistry*, 32(42):11385-89 (1993).

Wade, W.S. et al., "Design of peptides that bind in the minor groove of DNA at 5'-(A,T)G(A,T)C(A,T)-3' sequences by a dimeric side-by-side motif." *J. Am. Chem. Soc.*, 114(23):8783-94 (1992).

Wade, W.S., "Sequence specific complexation of B DNA at sites containing G,C base pairs." Ph.D. Thesis, California Institute of Technology, Pasadena, CA (1989).

White, S. et al., "Recognition of the four Watson-Crick base pairs in the DNA minor groove by synthetic ligands." *Nature*, 391:468-71 (1998).

White, S. et al., "On the pairing rules for recognition in the minor groove of DNA by pyrrole-imidazole polyamides." *Chemistry & Biology*, 4:569-578 (1997).

Xie, G. et al., "Protein kinase C-α Inhibitors; structure-activity relationships in bis-indole series." *Bioorg. Med. Chem. Lett.*, 5(5):497-500 (1995).

Xie, G. et al., Synthesis and DNA cleaving properties of hybrid molecules containing propargylic sulfones and minor groove binding lexitropsins. *Bioorg. Med. Chem. Lett.*, 3(8):1565-70 (1993).

Xue, C.B. et al, "Synthesis and Antiplatelet Effects of An Isoxazole Series of Glycoprotein llb/llla Antagonists", *Bioorg. Med. Chem. Lett.*, 8:3499-3504 (1998).

Yamori, T. et al., "Potent antitumor activity of MS-247, a novel DNA minor groove binder, evaluated by an in vitro and in vivo human cancer cell line panel." *Cancer Res.*, 59(16):4042-49 (1999).

Zakrzewska, K. et al., "Drug recognition of DNA. Proposal for GC minor groove specific ligands: vinylexins." *J. Biomol. Struct. Dyn.*, 6(2):1043-1058 (1989).

Zakrzewska, K. et al., "Theoretical study of the sequence selectivity of isolexins, isohelical DNA groove binding ligands. Proposal for the GC minor groove specific compounds." *J. Biomol. Struct. Dyn.*, 5(5):1043-1058 (1988).

21 X = Y = Z = C
22 X = N; Y = Z = C
23 Y = N; X = Z = C
24 X = Z = N; Y = C

A-1   X = Y = Z = C
A-12  X = N; Y = Z = C
A-13  Y = N; X = Z = C
A-15  X = Z = N; Y = C

26 R = OEt  ⎤ NaOH (aq.)
27 R = OH   ⎦ EtOH

ANTI-INFECTIVE BIARYL COMPOUNDS

CROSS-REFERENCES TO RELATED APPLICATIONS

This application claims the benefit of U.S. Provisional Application Ser. No. 60/421,438, filed Oct. 25, 2002, the content which is incorporated herein by reference.

BACKGROUND OF THE INVENTION

1. Field of the Invention

This invention relates to aromatic compounds having antibacterial activity and methods for their synthesis and use.

2. Description of Related Art

The discovery of penicillin and other antimicrobials in the early and mid-20th century generated a period of optimism about the medical profession's ability to treat microbial infections. However, the evolution of drug-resistant microbe strains—with new ones being constantly discovered has led to an appreciation of the continuing need to develop new antimicrobials, preferably ones that are structurally different from extant ones or employ a different mechanism of action.

Exemplary recent disclosures of new antibacterial compounds include Ge et al., WO 01/74898 (2001); Baird et al., U.S. application Ser. No. 10/132,887, filed Apr. 24, 2002; Bürli et al., U.S. application Ser. No. 10/165,856, filed Jun. 6, 2002; McMinn et al., U.S. application Ser. No. 10/165,433, filed Jun. 6, 2002 ("McMinn '433"); Bürli et al., U.S. application Ser. No. 10/165,857, filed Jun. 6, 2002; Bürli et al., U.S. application Ser. No. 10/165,764, filed Jun. 6, 2002; and Bürli et al., U.S. Provisional Application No. 60/400,671, filed Aug. 2, 2002. Matsunaga et al., U.S. Pat. No. 5,808,087 (1998), U.S. Pat. No. 5,821,258 (1998), U.S. Pat. No. 5,852,011 (1998) ("Matsunaga '011"); JP 11-171886; and JP 11-89594 also disclose compounds reportedly having antimicrobial activity.

Especially noteworthy are McMinn '433 and Matsunaga '011, each of which discloses as anti-microbial agents pyrrole-benzimidazole compounds characterized by a carboxy amide (—C(=O)NH—) or carboxy ester (—C(=O)O—) group attached to the 6-member ring of the benzimidazole ring system.

BRIEF SUMMARY OF THE INVENTION

The present invention provides novel biaryl antiinfective compounds, in which a pyrrole ring is directly bonded to a 6,5-condensed ring system, which can be but is not necessarily a benzimidazole system. Thus, this invention provides a compound according to formula (1)

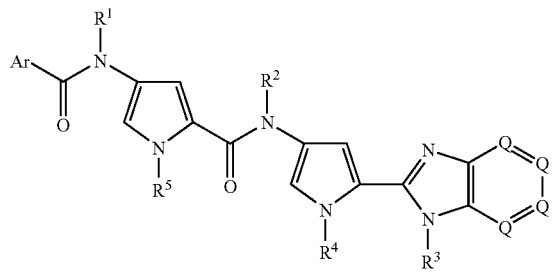

and the solvates, prodrugs, and pharmaceutically acceptable salts thereof, wherein Ar is an unsubstituted or substituted phenyl group, 5-member heteroaryl group, 6-member heteroaryl group, 6,6-condensed ring aryl or heteroaryl group, or 6,5-condensed ring heteroaryl group;

each Q is independently N, CH, C($R^6$), where $R^6$ is as defined hereinbelow, with the proviso that no more than two Q's are N;

each of $R^1$, $R^2$, $R^3$, and $R^4$ independently is H or a ($C_1$-$C_5$) alkyl group;

each $R^5$ is independently H, a substituted or unsubstituted ($C_1$-$C_{12}$) alkyl group, or a substituted or unsubstituted ($C_1$-$C_{12}$)heteroalkyl group; and each $R^6$ is independently a substituted or unsubstituted ($C_1$-$C_{12}$) alkyl, $OR^5$, $N(R^5)_2$, $O(CO)R^5$, $N(CO)R^5$, Cl, F, or Br.

DETAILED DESCRIPTION OF THE INVENTION

Abbreviations and Definitions

Figure 1:
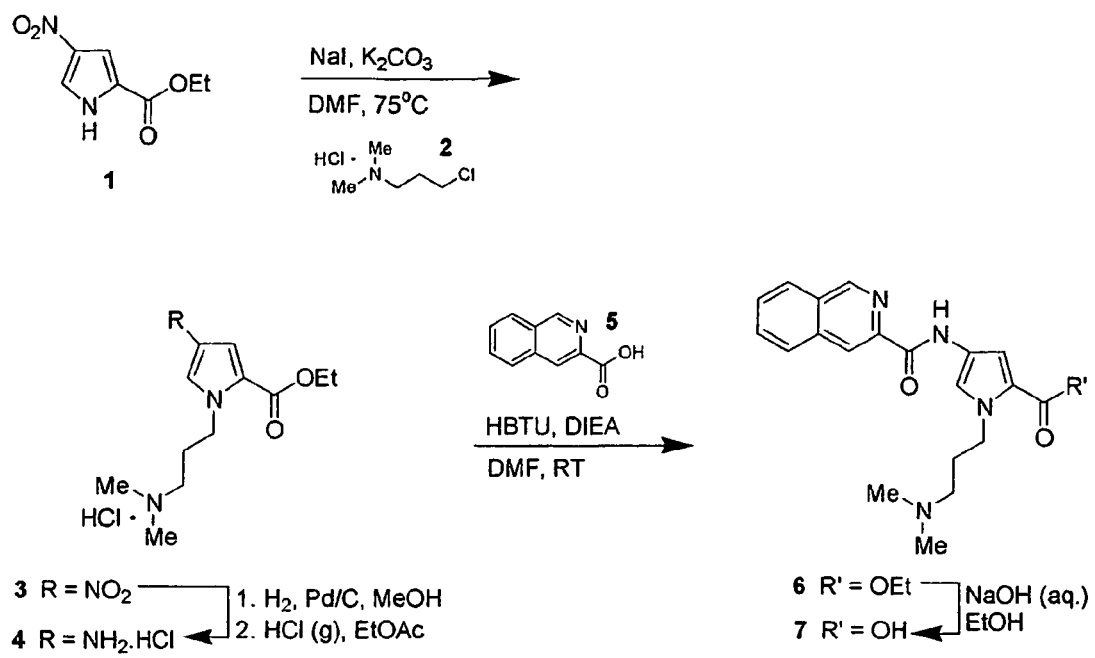
FIGS. 1-26 show chemical reactions used to make compounds of this invention.

The term "alkyl," by itself or as part of another substituent, means, unless otherwise stated, a straight or branched chain, or cyclic hydrocarbon radical, or combination thereof, which may be fully saturated, mono-or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having six or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be heteroatoms. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified by —CH$_2$—CH$_2$—S—CH$_2$CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "Cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-pipe-ridinyl, 2-piperidinyl, 3-piperidinyl, 4-morpholinyl, 3-morpholinyl, telraltydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$) alkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). Each of the above terms (e.g., "alkyl," heteroalkyl," "aryl" and "heteroaryl") are meant to include both substituted and unsubstituted forms of the indicated radical. Preferred substituents for each type of radical are provided below.

Substituents for the alkyl, heteroalkyl, aryl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', —N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R', —NR—C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R'" each independently refer to hydrogen, unsubstituted (C$_1$-C$_8$) alkyl and heteroalkyl, unsubstituted aryl, aryl substituted with 1-3 halogens, unsubstituted alkyl, alkoxy or thioalkoxy groups, or aryl-(C$_1$-C$_4$) alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as halo-alkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like) which are also preferred and contemplated by the present invention.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —S(O)$_2$R', —NH—C(NH$_2$)=NH, —NR'C(NH$_2$)=NH, —NH—C(NH$_2$)=NR', —S(O)R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, (C$_1$-C$_4$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

Two of the substituents on adjacent atoms of the aryl or heteroaryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)e-X—(CH$_2$)r, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulftric, hydriodic, or phosphorous acids and the like, as well as the salts derived from relatively nontoxic organic acids like acetic, ascorbic, propionic, isobulyric, malcic, malonic, lactic, malie, glutamic, benzoic, succinic, suberic, fumaric, mandelic, phthalic, benzenesulfonic, p-tolylsulfonic, citric, tartaric, methanesulfonic, lactobionic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (chiral centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Compounds

The present invention provides novel biaryl antiinfective compounds, in which a pyrrole ring is directly bonded to a 6,5-condensed ring system. An exemplary 6,5-condensed ring system is a benzimidazole system. Thus, this invention provides a compound according to formula (I)

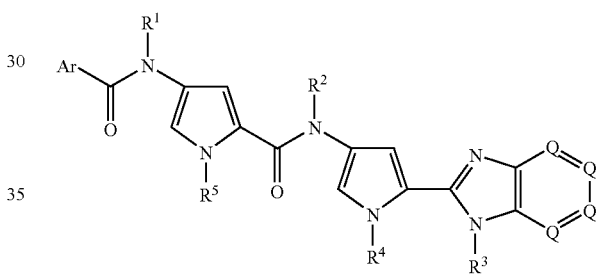

(I)

and the solvates, prodrugs, and pharmaceutically acceptable salts thereof, wherein Ar is an unsubstituted or substituted phenyl group, 5-member heteroaryl group, 6-member heteroaryl group, 6,6-condensed ring aryl or heteraryl group, or 6,5-condensed ring heteroaryl group;

each Q is independently N, CH, C(R$^6$), where R$^6$ is as defined hereinbelow, with the proviso that no more than two Q's are N;

each of R$^1$, R$^2$, R$^3$, and R$^4$ independently is H or a (C$_1$-C$_5$) alkyl group;

each R$^5$ is independently H, a substituted or unsubstituted (C$_1$-C$_{12}$)alkyl group, or a substituted or unsubstituted (C$_1$-C$_{12}$) heteroalkyl group; and each R$^6$ is independently a substituted or unsubstituted (C$_1$-C$_{12}$)alkyl, OR$^5$, N(R$^5$)$_2$, O(CO)R$^5$, N(CO)R$^5$, Cl, F, or Br.

Exemplary suitable R$^1$, R$^2$, R$^3$, and R$^4$ are H, methyl, ethyl, propyl, n-propyl, isopropyl, butyl, isobutyl, 2-butyl, t-butyl, n-propyl, 2-propyl, and 3-propyl. Preferably, R$^1$, R$^2$, R$^3$, and R$^4$ are H or methyl, with H being especially preferred in the instance of R$^1$, R$^2$, and R$^3$ and methyl being especially preferred in the instance of R$^4$.

In one group of preferred embodiments, R$^1$, R$^2$, and R$^3$ are each H and R$^4$ is methyl, i.e., as represented by formula (II)

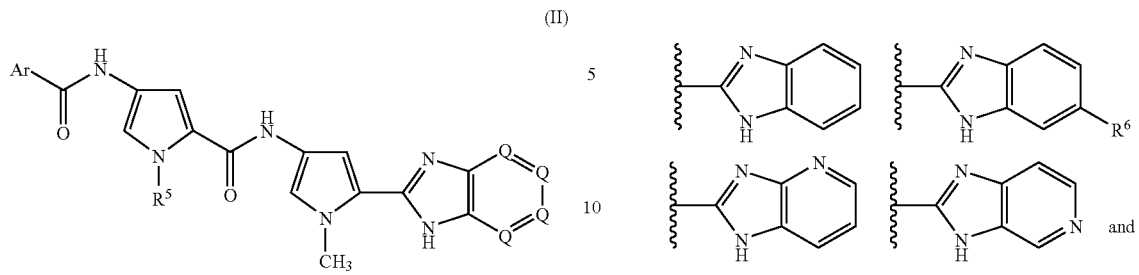

where Q and R⁵ are as previously defined.

Ar can be an unsubstituted or substituted (a) phenyl group;
(b) 5-member heteroaryl group, such as an imidazolyl, pyrrolyl, pyrazolyl, furanyl, isothiazolyl, oxazolyl, isoxazolyl, thiazolyl, furazanyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,3,4-oxadiazolyl, 1,2,4-oxadiazolyl, or thienyl group;
(c) 6-member heteroaryl group, such as a pyridyl, pyrimidyl, pyraeinyl pyridazinyl, or triazinyl group;
(d) 6,6-condensed ring aryl or heteroaryl group, such as a naphthyl, quinolyl or isoquinolyl group; or
(e) 6,5-condensed ring heteroaryl group, such as a benzothienyl, indolyl, or benzofuranyl group.

Preferably Ar is selected from the group consisting of

Preferred embodiments of the 6,5-condensed ring system in compounds of formulae (I) and (II), include:

In a preferred embodiment, at least one Q is N.

Combinations of the foregoing condensed 6,5 ring systems in preferred embodiments of compound I are represented in formulae (III) through (VII), where Ar, R⁵, and R⁶ are as previously defined:

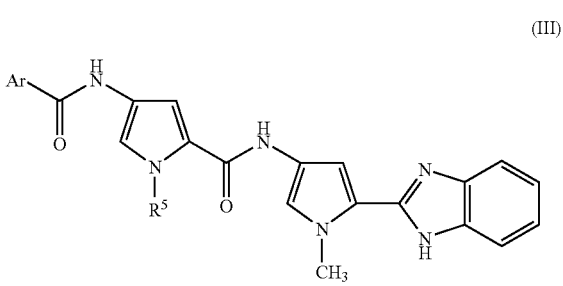

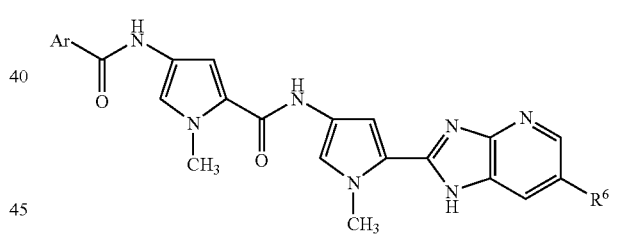

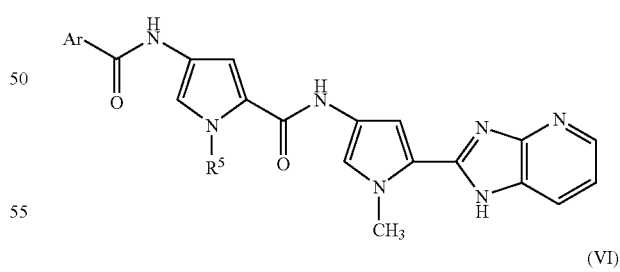

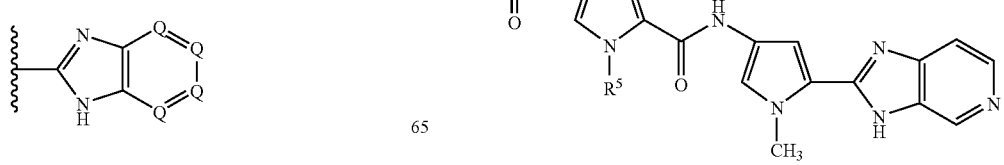

-continued (VII)

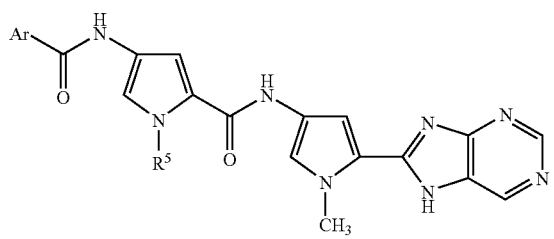

R⁵ preferably is a lower alkyl group such as methyl (especially), ethyl, propyl or isopropyl, $(CH_2)_n(Am)$, or $(CH_2)_n(OH)$, where n is 2, 3, 4, or 5 (especially 3) and Am is an alkyl amine group or a quaternary ammonium group. Examples of preferred R⁵'s include:

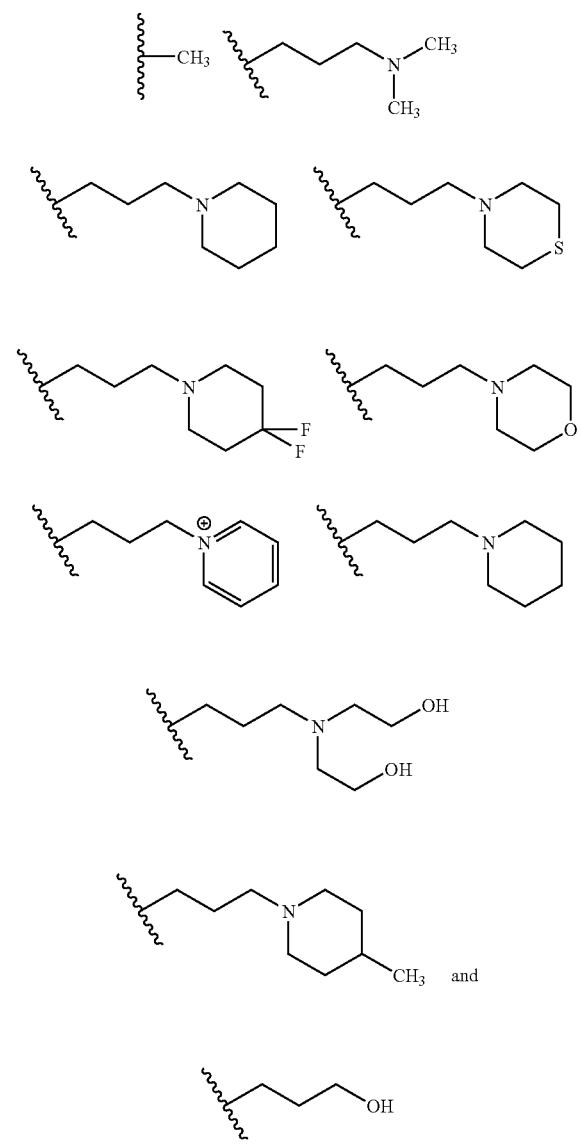

In a preferred embodiment of compound (I), R⁵ is methyl, Ar is

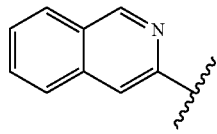

and in the condensed 6,5 ring system

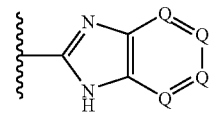

at least one Q is N and the remaining Q's are CH.

In another preferred embodiment of compound (I), Ar is selected from the group consisting of

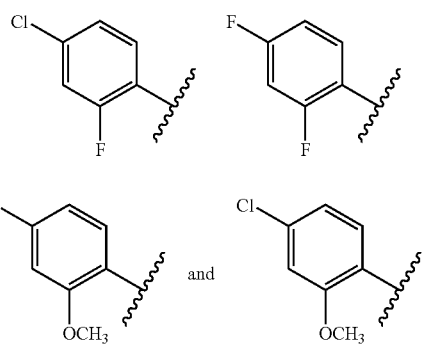

and R⁵ is $(CH_2)_3N(CH_3)_2$.

R⁶ preferably is a lower alkyl group such as methyl (especially), ethyl, propyl or isopropyl, OR⁵, NH(CO)R⁵, O(CO)R⁵, N(R⁵), or Cl. Examples of preferred R⁶'s include:

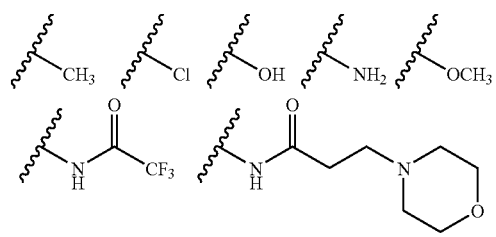

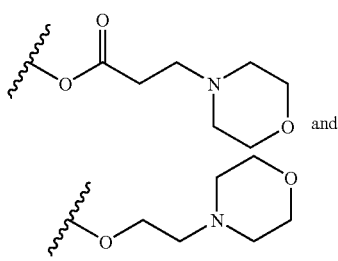

Exemplary specific compounds (I) are listed in Table A (wherein each R¹, R², and R³ is H and each R⁴ is methyl).

TABLE A

Exemplary Compounds (I)

| Ref. No. | Ar | R⁵ | (benzimidazole group) |
|---|---|---|---|
| A-1 | isoquinolin-3-yl | –(CH₂)₃–N(CH₃)₂ | 1H-benzimidazol-2-yl |
| A-2 | Same | –CH₃ | 5-methyl-1H-benzimidazol-2-yl |
| A-3 | Same | Same | 4-methyl-1H-benzimidazol-2-yl |
| A-4 | Same | Same | 5-methoxy-1H-benzimidazol-2-yl |
| A-5 | Same | Same | 5-(trifluoroacetylamino)-1H-benzimidazol-2-yl |
| A-6 | Same | Same | 5-hydroxy-1H-benzimidazol-2-yl |
| A-7 | Same | Same | 5-chloro-1H-benzimidazol-2-yl |
| A-8 | Same | Same | 5-amino-1H-benzimidazol-2-yl |
| A-9 | Same | Same | 5-(3-morpholinopropanoyloxy)-1H-benzimidazol-2-yl |
| A-10 | Same | –CH₃ | 5-(2-morpholinoethoxy)-1H-benzimidazol-2-yl |

TABLE A-continued

Exemplary Compounds (I)

| Ref. No. | Ar—⌇ | ⌇—R⁵ | ⌇—[heterocycle with Q atoms] |
|---|---|---|---|
| A-11 | Same | Same | ⌇—benzimidazol-2-yl with 5-NHC(O)CH₂CH₂-morpholine |
| A-12 | Same | ⌇—(CH₂)₃—N(CH₃)₂ | ⌇—imidazo[4,5-b]pyridin-2-yl |
| A-13 | Same | Same | ⌇—imidazo[4,5-c]pyridin-2-yl |
| A-14 | Same | ⌇—CH₃ | Same |
| A-15 | Same | ⌇—(CH₂)₃—N(CH₃)₂ | ⌇—imidazo[4,5-d]pyrimidin-2-yl |
| A-16 | 2,4-difluorophenyl | Same | ⌇—benzimidazol-2-yl |
| A-17 | Same | Same | ⌇—imidazo[4,5-b]pyridin-2-yl |
| A-18 | Same | Same | ⌇—imidazo[4,5-c]pyridin-2-yl |
| A-19 | Same | Same | ⌇—imidazo[4,5-d]pyrimidin-2-yl |
| A-20 | 4-fluoro-2-methoxyphenyl | ⌇—(CH₂)₃—N(CH₃)₂ | ⌇—benzimidazol-2-yl |

TABLE A-continued

Exemplary Compounds (I)

| Ref. No. | Ar— | —R⁵ | imidazole-Q group |
|---|---|---|---|
| A-21 | 4-Cl, 2-OCH₃ phenyl | Same | Same |
| A-22 | 3-chloro-benzothiophen-2-yl | Same | Same |
| A-23 | Same | -(CH₂)₃-piperidin-1-yl | Same |
| A-24 | Same | -(CH₂)₃-thiomorpholin-4-yl | Same |
| A-25 | Same | -(CH₂)₃-(4,4-difluoropiperidin-1-yl) | Same |
| A-26 | Same | -(CH₂)₃-morpholin-4-yl | Same |
| A-27 | Same | -(CH₂)₃-pyridinium | Same |
| A-28 | Same | -(CH₂)₃-N(CH₃)₂ | imidazo[4,5-b]pyridine |
| A-29 | Same | Same | imidazo[4,5-c]pyridine |
| A-30 | 3-chloro-benzothiophen-2-yl | -(CH₂)₃-N(CH₃)₂ | imidazo[4,5-d]pyrimidine |

TABLE A-continued

Exemplary Compounds (I)

| Ref. No. | Ar— | —R⁵ | (imidazole-Q ring) |
|---|---|---|---|
| A-31 | 4-Cl, 2-F phenyl | Same | 1H-benzimidazol-2-yl |
| A-32 | Same | 4-(piperidin-1-yl)butyl | Same |
| A-33 | Same | 4-(thiomorpholin-4-yl)butyl | Same |
| A-34 | Same | 4-(4-hydroxypiperidin-1-yl)butyl | Same |
| A-35 | Same | 4-(4,4-difluoropiperidin-1-yl)butyl | Same |
| A-36 | Same | 4-[bis(2-hydroxyethyl)amino]butyl | Same |
| A-37 | Same | 4-(morpholin-4-yl)butyl | Same |
| A-38 | Same | 4-(4-methylpiperidin-1-yl)butyl | Same |
| A-39 | Same | 4-(dimethylamino)butyl | 1H-imidazo[4,5-b]pyridin-2-yl |
| A-40 | Same | 4-(morpholin-4-yl)butyl | Same |

TABLE A-continued

Exemplary Compounds (I)

| Ref. No. | Ar— | —R⁵ | (heterocycle) |
|---|---|---|---|
| A-41 | 4-Cl, 2-F phenyl | -(CH₂)₃-N(4-methylpiperidine) | 1H-imidazo[4,5-b]pyridin-2-yl |
| A-42 | Same | -(CH₂)₃-N(4-hydroxypiperidine) | Same |
| A-43 | Same | -(CH₂)₃-N(4,4-difluoropiperidine) | Same |
| A-44 | Same | -(CH₂)₃-N(CH₂CH₂OH)₂ | Same |
| A-45 | Same | -(CH₂)₃-N(CH₃)₂ | 1H-imidazo[4,5-c]pyridin-2-yl |
| A-46 | Same | —CH₃ | 1H-imidazo[4,5-d]pyrimidin-2-yl (purine) |
| A-47 | 3-chlorothiophen-2-yl | Same | 1H-benzimidazol-2-yl |
| A-48 | Same | -(CH₂)₃-OH | Same |
| A-49 | Same | -(CH₂)₃-piperidin-1-yl | Same |
| A-50 | Same | -(CH₂)₃-morpholin-4-yl | Same |

TABLE A-continued

Exemplary Compounds (I)

| Ref. No. | Ar | R⁵ | (imidazole fused ring) |
|---|---|---|---|
| A-51 | 3-chloro-thiophen-2-yl | -(CH₂)₄-thiomorpholin-4-yl | 1H-benzimidazol-2-yl |
| A-52 | Same | -(CH₂)₄-(4-methylpiperidin-1-yl) | Same |
| A-53 | Same | -(CH₂)₄-(4-hydroxypiperidin-1-yl) | Same |
| A-54 | Same | -(CH₂)₄-(4,4-difluoropiperidin-1-yl) | Same |
| A-55 | Same | -(CH₂)₄-N(CH₂CH₂OH)₂ | Same |
| A-56 | Same | -(CH₂)₄-pyridinium | Same |
| A-57 | Same | -(CH₂)₄-N(CH₃)₂ | 1H-imidazo[4,5-b]pyridin-2-yl |
| A-58 | Same | -(CH₂)₄-piperidin-1-yl | Same |
| A-59 | Same | -(CH₂)₄-morpholin-4-yl | Same |
| A-60 | Same | -(CH₂)₄-thiomorpholin-4-yl | Same |

TABLE A-continued

Exemplary Compounds (I)

| Ref. No. | Ar— | —R⁵ | (imidazole-Q ring) |
|---|---|---|---|
| A-61 | Same | (propyl-N-piperidine with gem-diF) | Same |
| A-62 | 3-Cl-thiophen-2-yl | propyl-pyridinium | imidazo[4,5-b]pyridine |
| A-63 | Same | propyl-N(CH₃)₂ | imidazo[4,5-d]pyrimidine |

Compounds of this invention have been found to have anti-bacterial and/or anti-fungal properties and therefore may be used for preventing and/or treating infections in eukaryotic organisms. For human anti-infective applications, an effective amount of a compound of this invention is used, optionally in combination with a pharmaceutically acceptable carrier. The composition may be dry, or it may be a solution. Treatment may be reactive, for combating an existing infection, or prophylactic, for preventing infection in an organism susceptible to infection. Preferably, compounds of this invention are used to treat infections by drug-resistant strains of bacteria, for example MRSA (methicillin resistant *S. aureus*), MRSE (methicillin resistant *S. epidermidis*), PRSP (penicillin resistant *S. pneumoniae*) or VRE (vancomycin resistant *Enterococci*). By "drug-resistant" it is meant that the bacteria are resistant to treatment with conventional antibiotics.

Host organisms that can be treated include eukaryotic organisms, in particular plants and animals. The plant may be an agriculturally important crop, such as wheat, rice, corn, soybean, sorghum, and alfalfa. Animals of interest include mammals such as bovines, canines, equines, felines, ovines, porcines, and primates (including humans). Accordingly, in another aspect of this invention, there is provided a method for treating a bacterial infection—particularly an infection by Grant-positive bacteria—comprising administering to a patient in need of such treatment an effective amount of compound (I). Compounds of this invention can be used in the preparation of a medicament for treating a bacterial or fungal infection in a mammal. The compounds may be administered orally, topically, parenterally (e.g., intravenously, subcutaneously, intraperitoneally, transdermally) or by inhalation.

The practice of our invention can be further understood by reference to the following examples, which are provided by way of illustration and not of limitation.

Synthesis—General Remarks

Common abbreviations and acronyms are employed for various chemicals and techniques, including: Boc for t-butyloxycarbonyl (and (Boc)₂O for the corresponding anhydride); DIEA for diisopropylethylamine; DMF for N,N-dimethylformamide; ESI-MS for electrospray ionization mass spectrometry; HBTU for 2-(1H-benzotriazole-1-yl)-1,1,3,3-tetramethyluronium hexafluorophosphate; ¹H-NMR for proton NMR; MsCl for mesyl chloride; RP-HPLC for reverse phase high pressure liquid chromatography; RT for room (ambient) temperature; TEA for triethylamine; and TLC for thin layer chromatography.

Typically, the structures of compounds were confirmed by ¹H-NMR and/or mass spectrometry. Where a parenthetical remark such as "¹H-NMR" or "mass spectrum" or "ESI-MS" follows a reference to a compound without any elaboration, it means that such spectrum was taken, was consistent with the assigned structure, and did not indicate the presence of significant impurities.

The skilled artisan will understand that: (a) an intermediate described in the context of the synthesis of a particular compound of this invention can also be used to make other compounds of this invention, *mutatis mutandis*; (b) in certain experimental sections only the preparation of an intermediate compound is described, because its incorporation into a final compound of this invention straightforwardly follows synthetic methodology described herein; and (c) for some reactions that recur herein, detailed reaction and work-up conditions sometimes are not provided in each instance in the interest of brevity and that the conditions described elsewhere in this application are adaptable to the instance at hand without undue experimentation.

Synthesis—General Procedures

The following general procedures are used frequently in the synthesis of compounds of this invention. This section describes each in detail. Subsequent recurrences are then simply referred to as "Procedure A," "Procedure B," etc.

Procedure A: Coupling of an Aryl Amine with an Aryl Acid

A mixture of the acid (1.2 eq.) and HBTU (1.15 eq.) in DMF/DIEA (3 eq, DIEA, ca. 3:1 DMF:DIEA by volume) was stirred at RT for 30 min. The amine (1.0 eq.) in DMF (ca. same volume) was added and the mixture stirred at RT for 2-16 hr. The mixture was added dropwise to ice-water containing 10% $K_2CO_3$ (ca. 40× reaction volume). The resulting precipitates were collected by filtration and dried. In cases where no precipitates formed, the solution was extracted with EtOAc (3×) and the combined organic phases were dried ($MgSO_4$) and concentrated. The resulting crude product was either used directly in the next step, or, in the case of a final product, purified by RP-HPLC (Hamilton PRP-1 column, $CH_3CN$/0.5% aq. AcOH, 0%, to 60% in 60 min). The purified product was characterized by $^1$H-NMR and ESI-MS.

Procedure B: Reduction of a Nitro Pyrrole to an Amino Pyrrole

A solution of the nitro pyrrole (1 eq.) in a solvent (typically EtOAc, MeOH, or DMF) was purged with nitrogen ($N_2$) gas for several minutes. Palladium on carbon (Pd/C) (0.05 eq. by weight) was added portion-wise while purging with $N_2$. The flask was sealed and evacuated. Hydrogen gas ($H_2$) was introduced using a balloon. The evacuation was repeated several times, each time followed by the introduction of $H_2$. The reaction was stirred under a $H_2$ atmosphere for several hours until TLC analysis showed complete consumption of starting material. The flask was then purged with $N_2$ before opening. The Pd/C was removed by filtration through Celite© filter media. The solvent was either removed to provide crude amino pyrrole (in the case of EtOAc and MeOH) or the solution of the product was used directly in the next step (in the case of DMF).

Procedure C: Saponification of an Aryl Ester to an Aryl Acid.

A mixture of the ester (1 eq.) and NaOH or KOH (ca. 0.5 g base per g ester) in water (ca. 1 g ester per 40 mL) and MeOH or EtOH (ca. 1 g ester per 20 mL) was stirred at 40-60° C. for 3-18 hr. The mixture was diluted with water (ca. 2× reaction volume), washed with HtOAc (1×) and acidified to pH 2-3 using ca. 6M aq. HCl. The resulting precipitates were collected by filtration and dried.

Procedure D: Mesylation of a Primary Alcohol and Substitution with an Amine

A mixture of the alcohol (1 eq.) and DIEA (3 eq.) in DMF (ca. 1 mL per 50 mg alcohol) was treated with mesyl chloride (1.2 eq.) at RT then stirred for 1 hr at 40° C. The amine (510 eq.) was added and the reaction mixture was stirred at 60° C. for 12 hr. After cooling, the reaction mixture was diluted with 40% aq. AcOH and purified by RP-HPLC (Hamilton PRP-1 column, $CH_3CN$/0.5% aq. AcOH, 0% to 60% in 60 min). The purified product was characterized by $^1$H-NMR and ESI-MS.

Synthesis—Specific Compounds

EXAMPLE A

Figure 2:
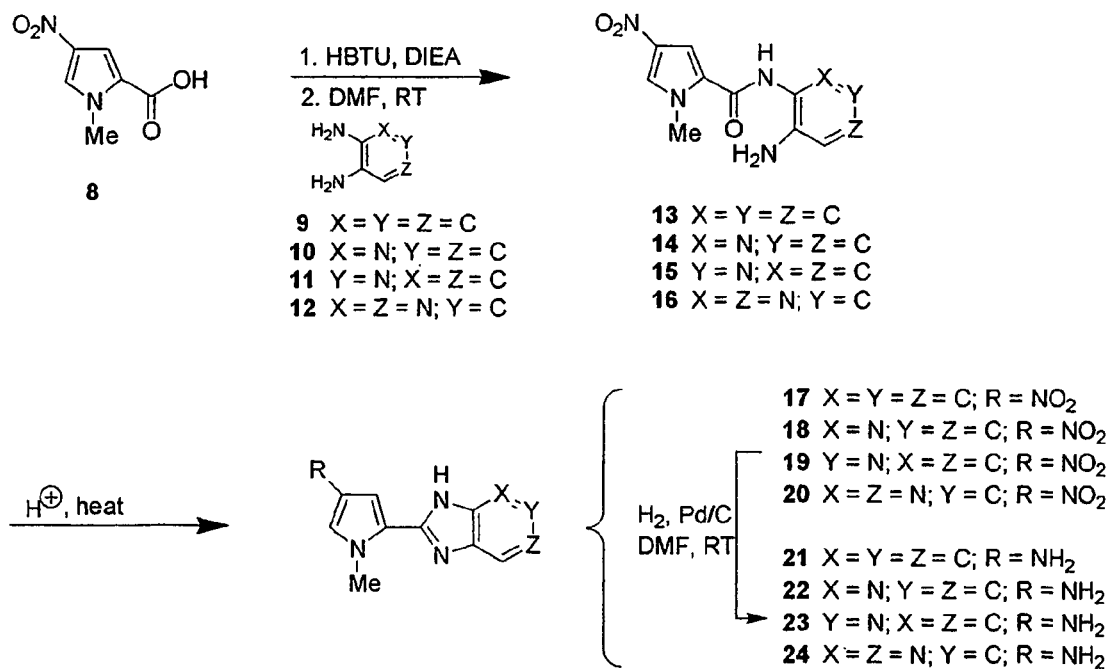
Figure 3:
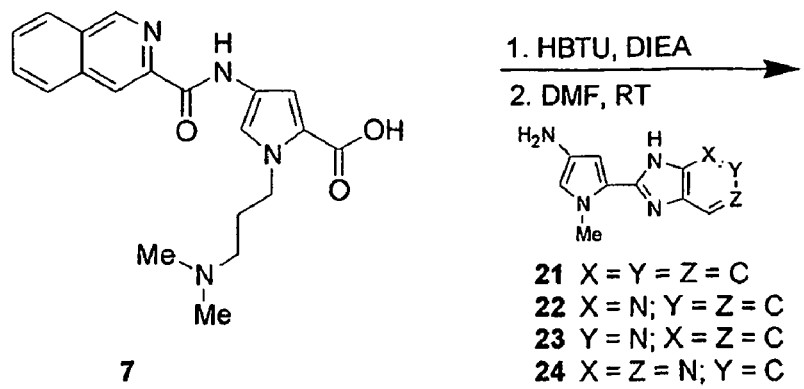
Figure 3:
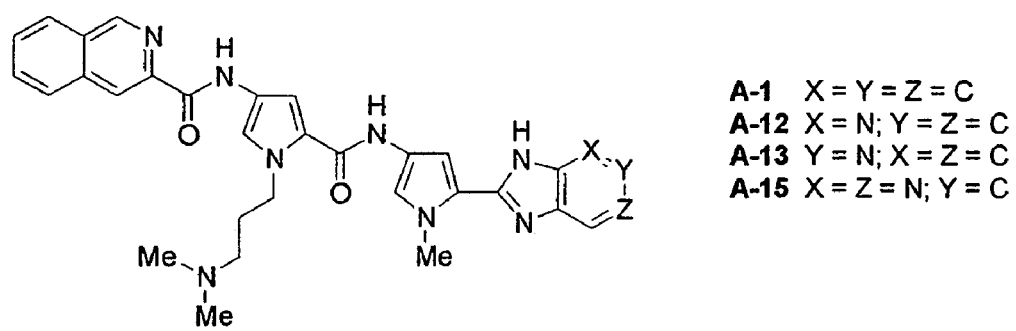

This example describes the synthesis of a subgenus of compounds (I) in which Ar is an isoquinoline group. The preparation of intermediate dimer acid 7 is shown in FIG. 1. FIG. 2 details the preparation of succeeding intermediate biaryl amines 21-24. The preparation of compounds A-1, A-12, A-13, and A-15 is outlined in FIG. 3.

Nitro pyrrole 3. A mixture of pyrrole 1 (10.0 g, 54.3 mmol), alkyl chloride 2 (9.44 g, 1.1 eq.), NaI (8.14 g, 1 equiv.), and $K_2CO_3$ (16.51 g, 2 eq.) in DMF (150 mL) was stirred at 75° C. for 16 hr. After cooling, the mixture was poured into 1M HCl (500 mL) and washed with EtOAc (2×300 mL). Solid $Na_2CO_3$ was added carefully to neutralize the acid and the solution extracted with EtOAc (3×300 mL). The organic layers were dried ($MgSO_4$) and evaporated to give nitro pyrrole 3 (7.77 g, 53%, $^1$H-NMR).

Amino pyrrole 4. Nitro pyrrole 3 (7.65 g, 28.4 mmol) was reduced according to Procedure B in MeOH. Following removal of solvent, the crude dark brown oil product was taken up in EtOAc (200 mL) and MeOH (10 mL) and cooled in an ice bath. HCl gas was bubbled through the solution for ca. 30 sec. Evaporation of solvents gave amino pyrrole 4 (8.05 g, 91%, yellow/brown solid, $^1$H-NMR).

Dimer ester 6. Pyrrole 4 (1.2 g, 3.85 mmol) was coupled to isoquinoline carboxylic acid 5 (0.8 g) according to Procedure A to give dimer ester 6 (1.35 g, 90%, $^1$H-NMR).

Dimer acid 7. Dimer ester 6 (1.30 g, 3.30 mmol) was saponified in NaOH/EtOH at 60° C. for 16 hr according to Procedure C, giving dimeric acid 7 (121 g, >95%, $^1$H-NMR)

Amides 13 to 16. Amides 13 to 16 were prepared by coupling nitro pyrrole carboxylic acid 8 (2.71 g, 15.9 mmol) with diamines 9 to 12 (1.1 equiv), respectively, according to Procedure A (~70% average yield).

Compounds 17 to 20. Cyclization of amides 13 to 16 to compounds 17 to 20 was achieved by heating in acid. Compound 13 (16.05 g, 61.67 mmol) was heated at 60° C. in glacial AcOH (200 mL) for 2 hr. The AcOH was evaporated and $Et_2O$ added to precipitate product 17, which was collected by filtration (7.82 g, 52%). Compound 14 (6.02 g, 23.1 mmol) was heated at reflux in glacial AcOH (200 mL) for 16 hr. Product 18 was collected in an analogous fashion to compound 17 (3.42 g, 61%). Compound 15 (7.31 g, 28.0 mmol) was heated at reflux in concentrated HCl for 16 hr. Evaporation of the solvent followed by addition of $Et_2O$ caused precipitation of product 19 (4.0 g, 59%). Compound 16 (5.8 g, 22.0 mmol) was treated analogously to compound 14, giving product 20 (2.74 g, 51%).

Amines 21 to 24. Reduction of the nitro group in compounds 17 to 20 was carried out according to Procedure B in DMF to provide the corresponding amines 21 to 24, which were used directly in the next step.

Compounds A-1, A-12, A-13, and A-15. Coupling of dimeric acid 7 (ca. 100 mg scale) with each of amines 21 to 24 was carried out according to Procedure A, providing the corresponding final products A-1, A-12, A-13, and A-15.

EXAMPLE B

Figure 4:
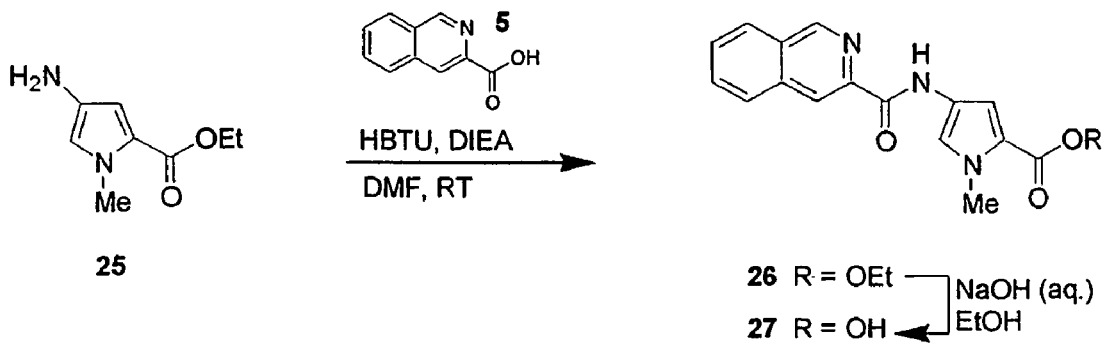
Figure 5:
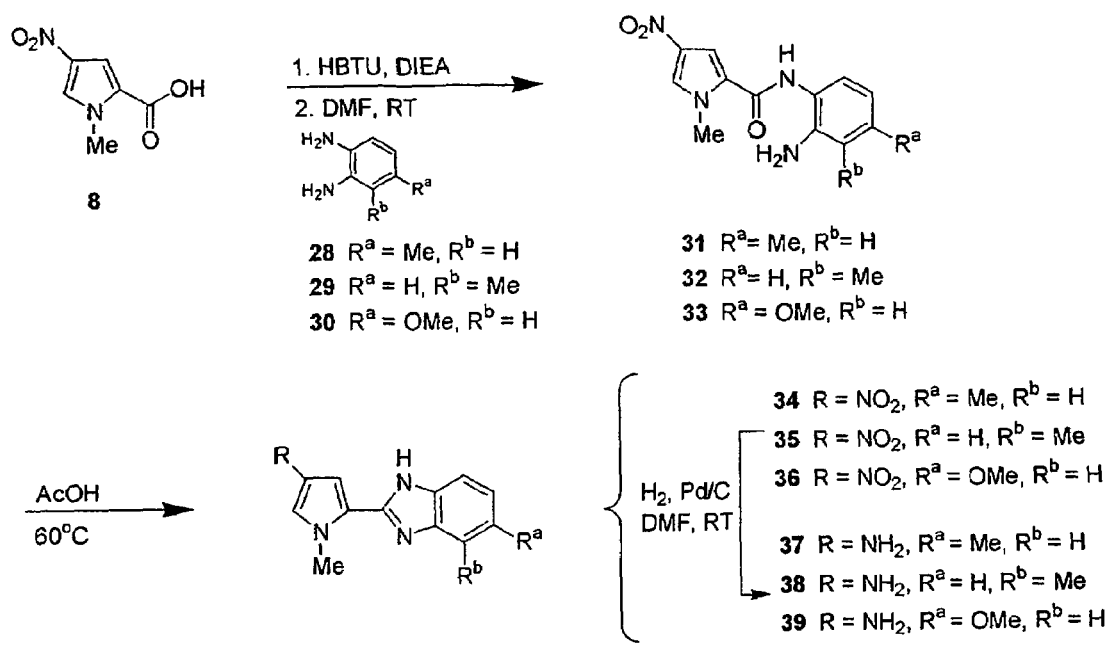
Figure 6:
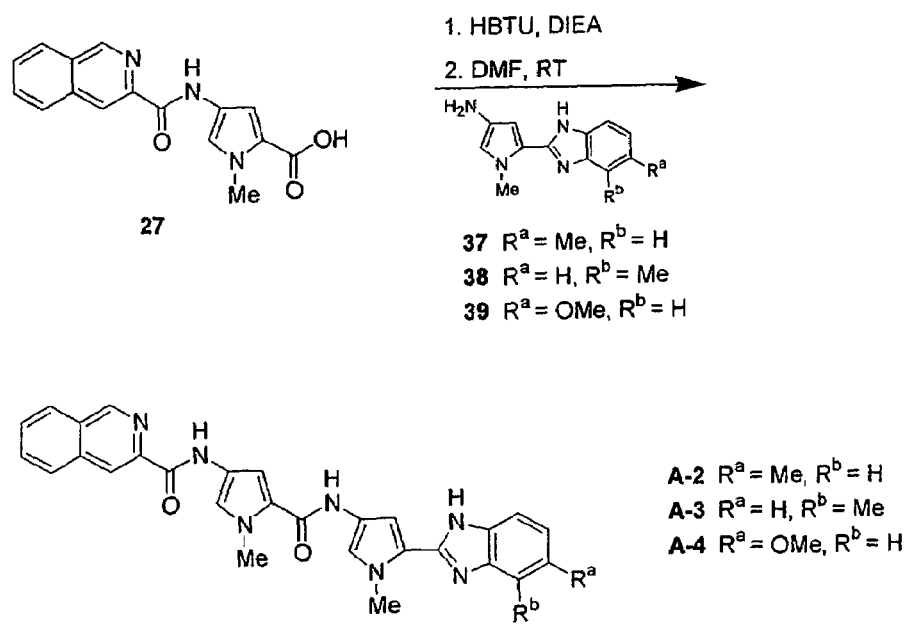

This example describes the synthesis of another subgenus of compounds (I) in which Ar is an isoquinoline group. The preparation of intermediate dimer acid 27 is shown in FIG. 4. FIG. 5 details the preparation of succeeding intermediate biaryl amines 37-39. The preparation of compounds A-2, A-3 and A-4 is outlined in FIG. 6.

Dimer ester 26 Amino pyrrole ester 25 (11.6 g, 68.97 turnoff was coupled to isoquinoline carboxylic acid 5 (14.3 g, 82.76 mmol) according to Procedure A to give dimer ester 26 (20.27 g, 91% $^1$H-NMR).

Diner acid 27. Saponification of ester 26 (19.5 g, 60.37 mmol) using NaOH in EtOH at 60° C. for 12 hr according to Procedure C gave dimer acid 27 (17.1 g, >95%, $^1$H-NMR).

Compounds 31 to 33. Compounds 31 to 33 were prepared by coupling carboxylic acid 8 (1.0 g, 5.88 mmol) with diamines 28 to 30 (6.46 mmol, 1.1 equiv), respectively, according to Procedure A (~85% average yield).

Compounds 34 to 36. Cyclization of compounds 31 to 33 (5 mmol scale) was achieved by heating at 60° C. in glacial AcOH (100 ml.) for 2 hr to provide compounds 34 to 36. The AcOH was evaporated and Et₂O added to precipitate the products, which were obtained by filtration and used without further purification (~60% average yield).

Amines 37 to 39. Reduction of the nitro group in compounds 34 to 36 was carried out according to Procedure B in DMF to provide corresponding amines 37 to 39, which were used directly in the next step.

Compounds A-2, A-3 and A-4. Coupling of dimeric acid 27 (ca. 100 mg scale) with amines 37 to 39 was carried out according to Procedure A, providing compounds A-2 to A-4.

EXAMPLE C

Figure 7:
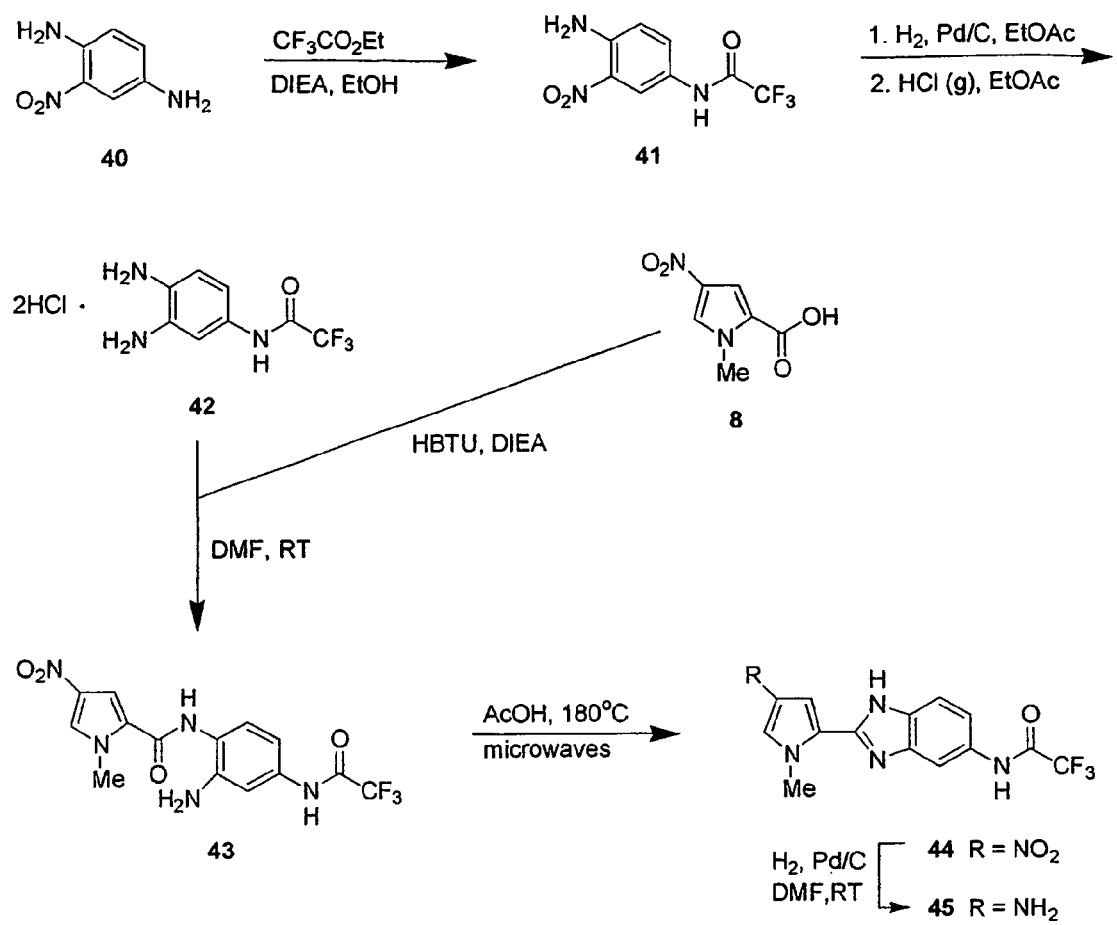
Figure 8:
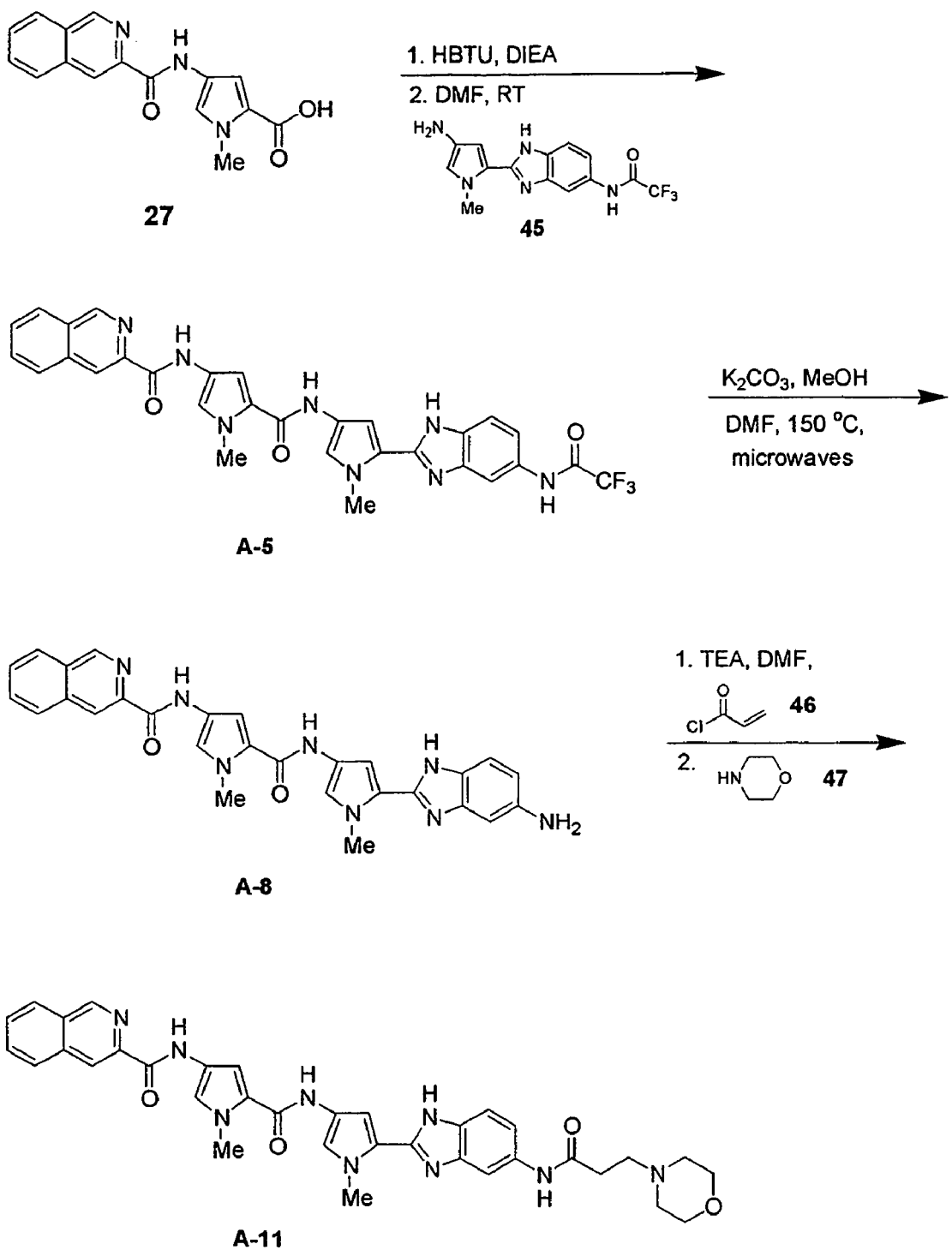

This example describes the synthesis of yet another subgenus of compounds (I) in which Ar is an isoquinoline group. FIG. 7 details the preparation of trifluoroacetamido intermediate 45. The preparation of compounds A-5, A-8 and A-11 is outlined in FIG. 8.

Compound 41. Nitro-diamine 40 (1.0 g, 6.53 mmol) was dissolved in EtOH (2-5 mL) and DIEA (2.3 mL, 13.06 mmol and the solution was cooled to 0° C. Ethyl trifluoroacetate (0.93 g 6.53 mmol) was added and the reaction was stirred at 0° C. for 1 hr. The cooling bath was then removed and the reaction stirred al room temperature for 12 hr. The solution was poured into 10% aqueous $K_2CO_3$ solution and extracted with EtOAc (2×100 mL). The organic layers were dried ($MgSO_4$) and evaporated to give compound 41 ($^1$H NMR) as a yellow oil, which was used directly in the next step without purification.

Diamine 42. The nitro group in compound 41 was reduced in EtOAC according to Procedure B. Following removal of the solvent, the crude dark brown oil product was taken up in EtOAc (25 mL) and cooled in an ice bath. HCl gas was bubbled through the solution for ca. 15 seconds. Addition of Et₂O caused precipitation of the dihydrochloride of diamine 42 (1.54 g, 81% over 2 steps, oil-white solid, $^1$H-NMR).

Compound 43. Coupling of carboxylic acid 8 (1.0 g, 5.88 mmol) with diamine 42 (1.5 g, 5.14 mmol) according to Procedure A gave compound 43 (1.04 g, 55%, $^1$H-NMR).

Compound 44. Compound 43 (0.85 g, 2.3 mmol) was dissolved in glacial acetic acid (4 mL) and heated to 180° C. by microwave irradiation for 5 min. The solvent was evaporated to leave compound 44 (0.8 g, >95%, $^1$H NMR), which was used without further purification.

Trifluoroacetamido intermediate 45. Reduction of the nitro group in compound 44 (0.5 g, 1.4 mmol) was carried out according to Procedure B in DMF to provide the trifluoroacetamido intermediate 45, which was used directly in the next step.

Compound A-5. Coupling of dimeric acid 27 (0.48 g, 1.62 mmol) with trifluoroacetamido intermediate 45 (1.4 mmol) in DMF according to Procedure A gave compound A-5.

Compound A-8. Compound A-5 (100 mg. 0.17 mmol) was dissolved in a mixture of DMF (1 mL) and MeOH (2 mL). Solid $K_2CO_3$ (3 eq.) was added and the reaction mixture heated to 150° C. by microwave irradiation for 5 min. After cooling, the reaction mixture was diluted with 40% aqueous AcOH (to 15 mL total volume) and the product obtained by HPLC purification (Hamilton PRP-1 column, $CH_3CN$/0.5% aq. AcOH, 0% to 60% in 60 min).

Compound A-11. Compound A-8 (20 mg, 0.04 mmol) was dissolved in a mixture of DMF (2 mL) and TEA (0.5 mL). The solution was cooled to 0° C. before addition of acryloyl chloride 46 (~10 mg). The reaction was stirred at 0° C. for 1 hr. Morpholine (47) was added arid the reaction stirred at room temperature for 2 hr. The reaction was diluted using 40% aqueous AcOH (to 15 mL total volume) and the product obtained by HPLC purification (Hamilton PRP-1 column, $CH_3CN$/0.5% aq. AcOH, 0% to 60% in 60 min).

EXAMPLE D

Figure 9:
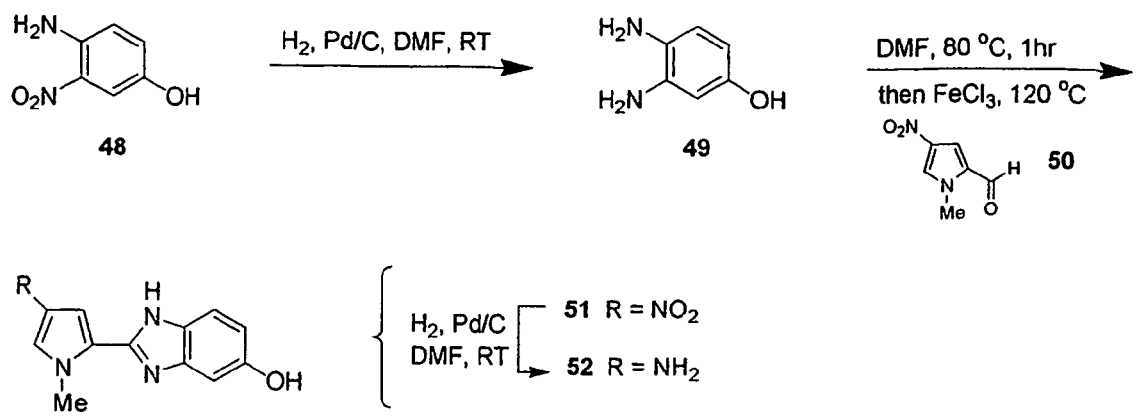
Figure 10:
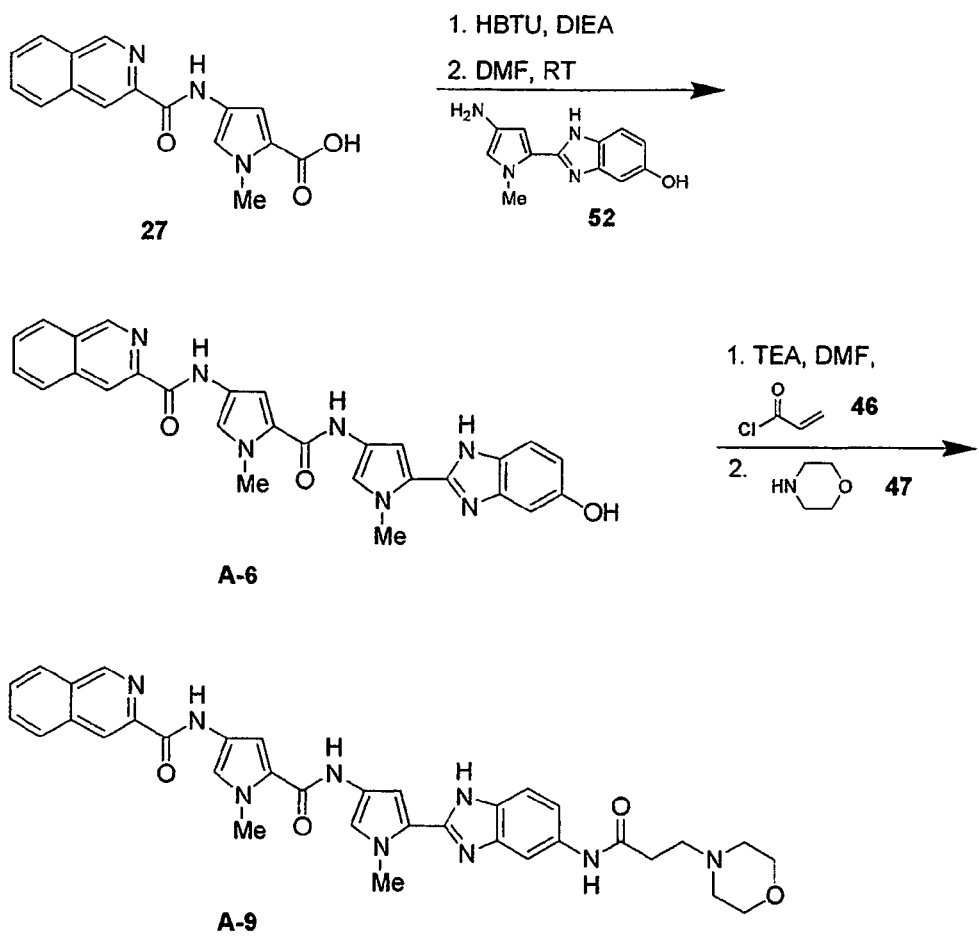

This example describes the synthesis of yet another subgenus of compounds (I) in which Ar is an isoquinoline group. FIG. 9 details the preparation of intermediate hydroxy amine 52. The preparation of the final compounds A-6 and A-9 is outlined in FIG. 10.

Diamine 49. Reduction of the nitro group in nitro amine 48 (1.0 g 6.49 mmol) was carried out according to Procedure B in DMF to provide a solution of diamine 49, which was used directly in the next step.

Compound 51. A mixture of diamine 49 (6.49 mmol) and aldehyde 50 (1.0 g, 6.49 mmol) in DMF (25 mL) was heated at 80° C. for 1 hr. Iron (III) chloride (0.21 g 1.30 mmol, 0.2 eq.) was added and the reaction heated at 120° C. for 12 hr in an open flask. After cooling, the mixture was added dropwise to vigorously stirred ice-cold water, causing precipitation of compound 51, collected by filtration and dried (1.46 g, 87%, ESI-MS, $^1$H NMR).

Hydroxy amine 52. Reduction of the nitro group in compound 51 (0.25 g, 0.97 mmol) was carried out according to Procedure B in DMF to provide a solution of hydroxy amine 52, which was used directly in the next step.

Compound A-6. Coupling of dimeric acid 27 (0.32 g, 1.10 mmol) with hydroxy amine 52 (0.97 mmol) in DMF according to Procedure A gave final product A-6.

Compound A-9. Compound A-6 (25 mg, 0.05 mmol) was dissolved in a mixture of DMF (2 mL) and TEA (0.5 mL). The solution was cooled to 0° C. before addition of the acid chloride 46 (~10 mg). The reaction mixture was stirred at 0° C. for 1 hr. Morpholine 47 was added and the reaction stirred at RT for 2 hr. The reaction mixture was with using 40% aq. AcOH (to 15 mL total volume) and compound A-9 was isolated by HPLC purification (Hamilton PRP-1 column, $CH_3CN$/0.5% aq. AcOH, 0% to 60%, in 60 min).

EXAMPLE E

Figure 11:
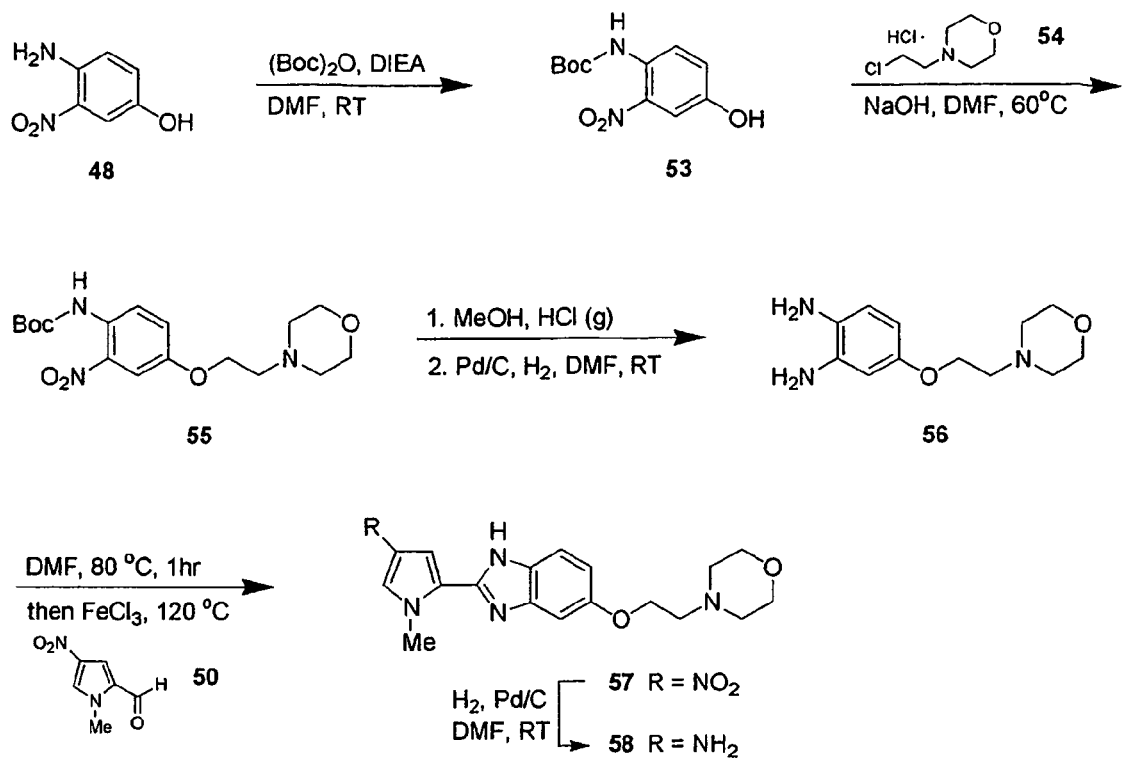
Figure 12:
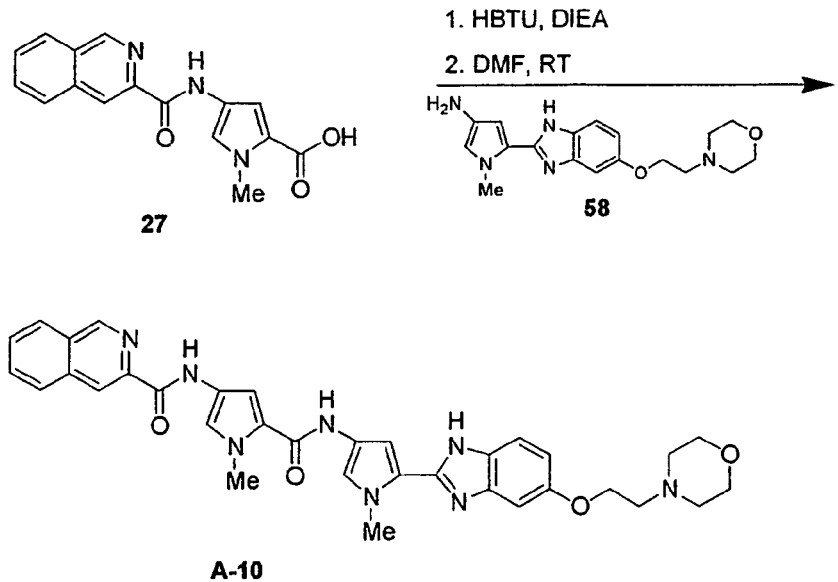

This example describes the synthesis of yet another subgenus of compounds (I) in which Ar is an isoquinoline group. FIG. 11 details the preparation of morpholino intermediate 58. The preparation of final compound A-10 is outlined in FIG. 12.

Phenol 53. Aminophenol 48 (1.0 g, 6.49 mmol) was dissolved in DMF (10 mL) and DIEA (2.26 mL, 12.98 mmol). A Solution of $(Boc)_2O$ (2.12 g, 9.73 mmol) in DMF (10 mL) was added dropwise at RT and the reaction left stirring for 16 hr. The mixture was added to vigorously stirred ice-cold water, causing precipitation of phenol 53, which was collected by filtration and dried (yellow solid, 1.52 g, 92%, $^1$H NMR).

Compound 55. Solid NaOH (0.32 g, 7.8 mmol) was added to a solution of phenol 53 (1.0 g, 3.9 mmol) in DMF (10 mL) and the reaction mixture was stirred at RT for 1 hr. Alkyl chloride 54 (0.80 g, 4.29 mmol) was added and the reaction mixture was heated at 60° C. for 16 hr. The reaction mixture was poured into 10% aq. $K_2CO_3$ (100 mL) and extracted with EtOAc (2×100 mL). The organic layers were dried ($MgSO_4$) and evaporated to give compound 55 ($^1$H NMR) as an oil, which was used directly in the next step without purification.

Diamine 56. Methanol (50 mL) was cooled to 0° C. and saturated with HCl (g). This solution was added to compound 55 (3.9 mmol) and the reaction stirred at RT for 1 hr. ESI-MS analysis showed complete removal of the Boc group. All volatile components were evaporated under high vacuum. The nitro group was then reduced according to Procedure B in DMF to provide a solution of diamine 56, which was used directly in the next step.

Compound 57. A mixture of diamine 56 (3.9 mmol and aldehyde 50 (0.6 g, 3.9 mmol) in DMF (15 mL) was heated at 80° C. for 1 hr. Iron (III) chloride (0.13 g, 0.78 mmol, 0.2 eq.) was added and the reaction heated at 120° C. for 12 hr in an open flask. After cooling, the mixture was added dropwise to a vigorously stirred solution of 10% $Na_2CO_3$ in ice-cold water, causing precipitation of compound 57, which was collected by filtration and dried (1.09 g, 75%, $^1$H NMR).

Molpholino intermediate 58. Reduction of the nitro group in compound 57 (0.1 g, 0.27 mmol) was carried out according to procedure B in DMF to provide a solution of morpholino intermediate 58, which was used directly in the next step.

Compound A-10. Coupling of dimeric acid 27 (0.091 g, 0.31 mmol) with morpholino intermediate 58 (0.27 mmol) in DMF according to Procedure A gave final product A-10.

EXAMPLE F

Figure 13:
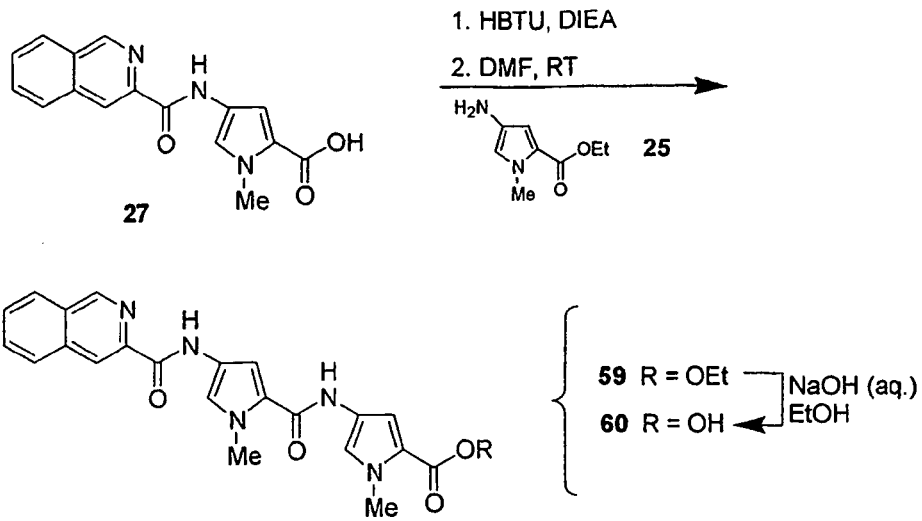
Figure 14:
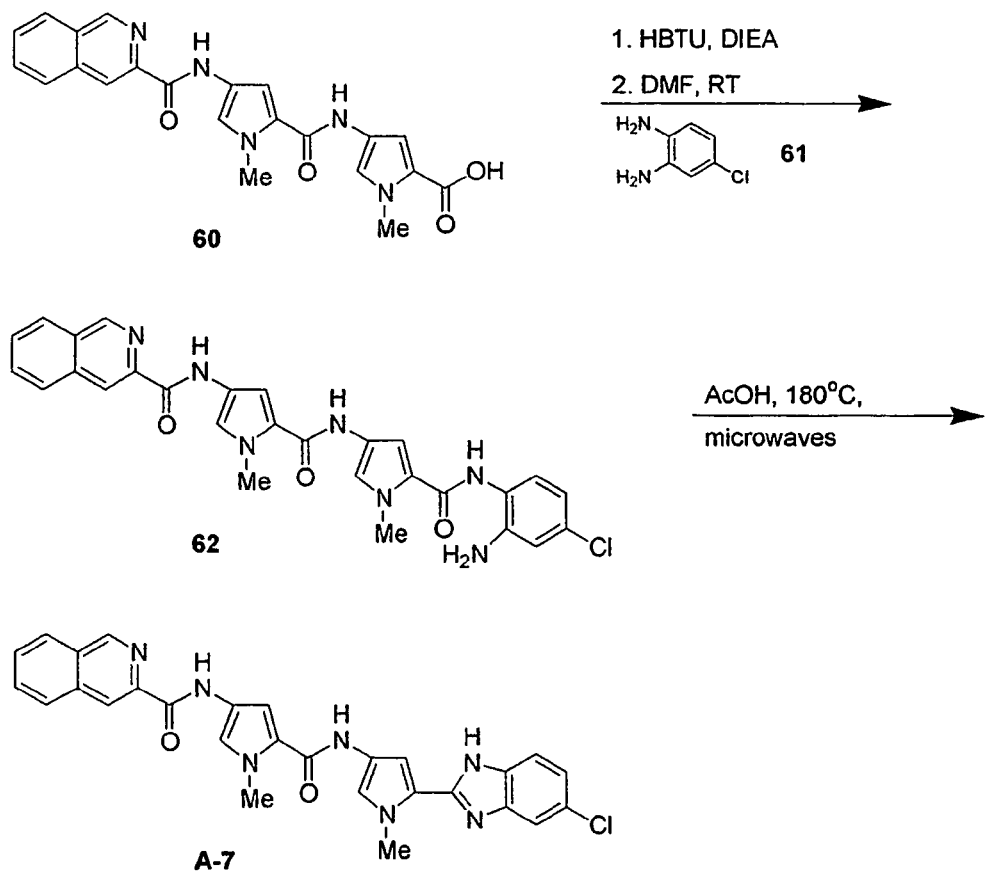

This example describes the synthesis of yet another subgenus of compounds (I) in which Ar is an isoquinoline group. FIG. 13 details the preparation of intermediate trimer acid 60. The preparation of the final compound A-7 is outlined in FIG. 14.

Trimer ester 59. Pyrrole 25 (5.4 g, 32.14 mmol) was coupled to dimer acid 27 (10.90 g, 36.96 mmol) according to Procedure A to give Trimer ester 59 (12.17 g, 85%, $^1$H-NMR).

Trimer acid 60. Saponification of trimer ester 59 (12.15 g, 27.32 mmol) using NaOH in EtOH at 60° C. for 12 hr according to Procedure C gave trimer acid 60 (10.94 g, >95%, $^1$H-NMR).

Compound 62. Chloro diamine 61 (0.36 g, 2.54 mmol) was coupled to trimer acid 60 (1.0 g, 2.4 turmoil according to Procedure A to give compound 62 (0.88 g, 68%, $^1$H-NMR).

Compound A-7. Compound 62 (0.21 g, 0.39 mmol) was dissolved in glacial AcOH (3 mL) and heated to 180° C. by microwave irradiation for 5 min. The solvent was evaporated and the residue diluted using 40% aq. AcOH (to 15 mL total volume) and compound A-7 obtained by HPLC purification (Hamilton PRP-1 column, $CH_3CN$/0.5% aq. AcOH, 0% to 60% in 60 min).

EXAMPLE G

Figure 15:
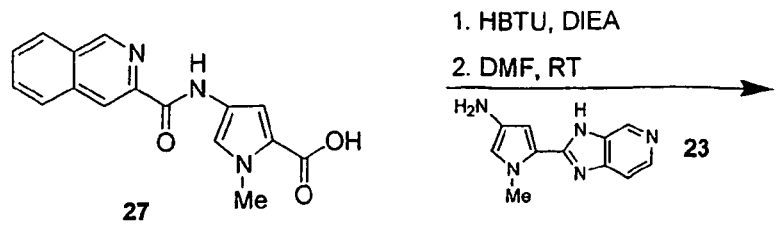
Figure 15:
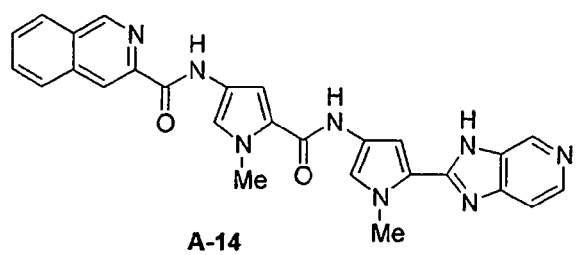

This example describes the synthesis of yet another subgenus of compounds (I) in which Ar is an isoquinoline group, as shown in FIG. 15 with reference to compound A-14.

Compound A-14. Dimeric acid 27 (0.20 g, 0.68 mmol) was coupled to amine 23 (0.145 g, 0.68 mmol) according to Procedure A, to give compound A-14.

EXAMPLE H

Figure 16:
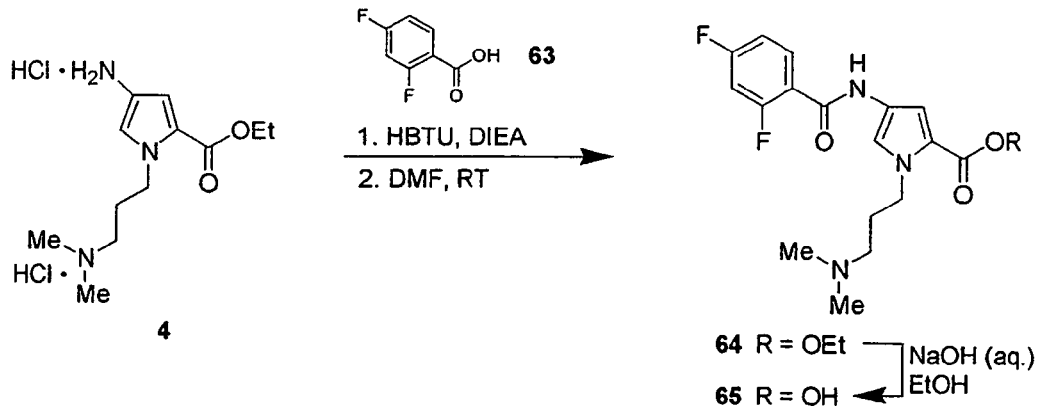
Figure 16:
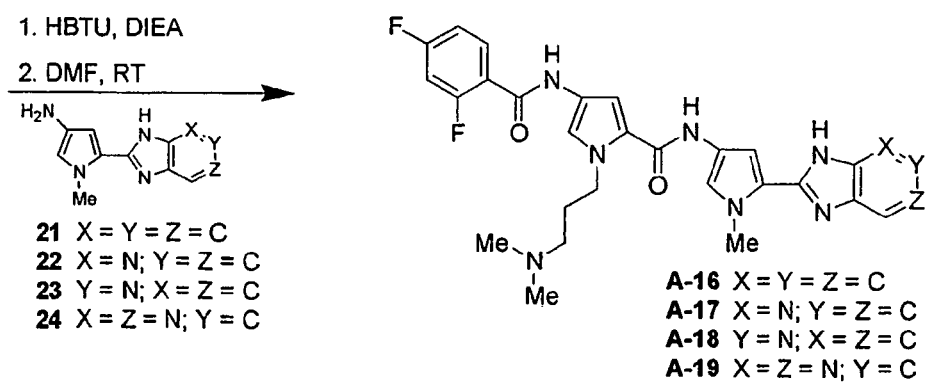

This example describes the synthesis of a subgenus of compounds (I) in which Ar is a difluorobenzene group. The preparation of intermediate diner acid 65 and its coupling with amines 21-24 in preparation of the final compounds A-16, A-17, A-18, and A-19 is outlined in FIG. 16.

Dimer ester 64. Pyrrole 4 (8.61 g, 27.56 tumult was coupled to difluorobenzoic acid 63 (5.2 g) according to Procedure A to give diner ester 64 (9.71 g, 93%, $^1$H-NMR).

Dimer acid 65. Dimer ester 64 (9.70 g, 25.59 mmol) was saponified using NaOH in EtOH at 60° C. for 16 hr according to Procedure C, giving dimer acid 65 (1.21 g, >95%, $^1$H-NMR).

Compounds A-16, A-17, A-18 and A-19. Coupling of dimer acid 65 (ca. 100 mg scale) with amines 21 to 24 was carried out according to Procedure A, providing respectively compounds A-16 to A-19.

EXAMPLE I

Figure 17:
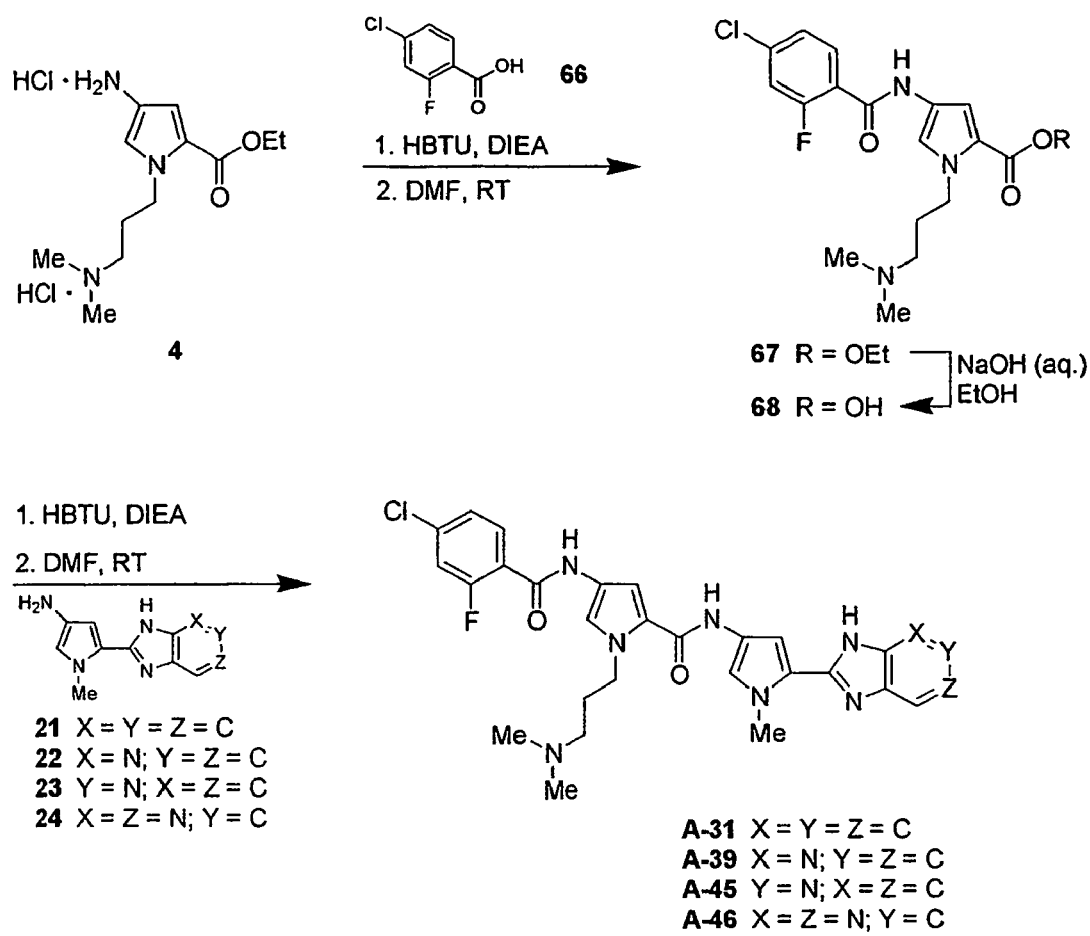

This example describes the synthesis of a subgenus of compounds (I) in which Ar is a 4-chloro-2-fluorobenzene group. The preparation of intermediate dimer acid 68 and its coupling with amines 21-24 to prepare compounds A-31, A-39, A-45, and A-46 is outlined in FIG. 17.

Dimer ester 67. Pyrrole 4 (10.26 g, 32.84 mmol) was coupled to 4-chloro-2-fluorobenzoic acid 66 (6.9 g) according to Procedure A to give dimer ester 67 (11.31 g, 87%, $^1$H-NMR).

Dimer acid 68. Dimer ester 67 (11.30 g, 28.57 mmol) was saponified using NaOH in EtOH at 60° C. for 16 hr according to Procedure C, giving dimer acid 68 (10.51 g, >95%, $^1$H-NMR).

Compounds A-31 A-39 A-45 and A-46. Coupling of Compound 68 (ca. 100 mg scale) with amines 21 to 24 was carried out according to Procedure A, providing compounds A-31, A-39, A-45, and A-46.

EXAMPLE J

Figure 18:
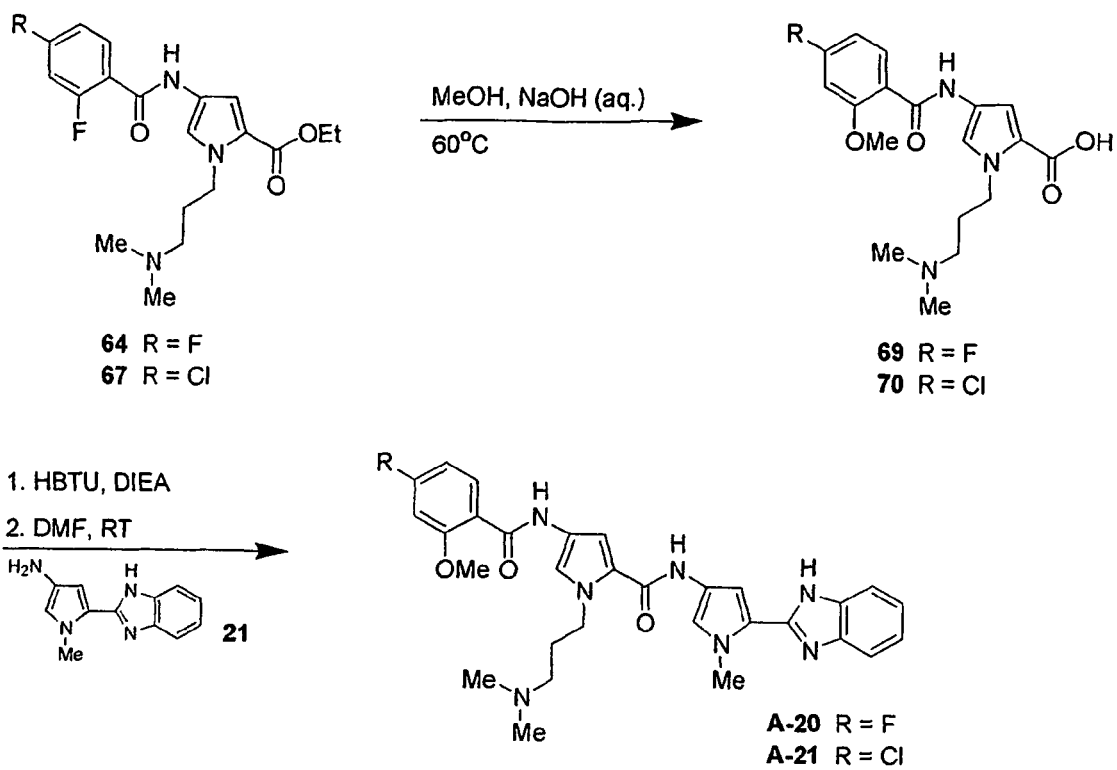

This example describes the synthesis of a subgenus of compounds (I) in which Ar is a methoxyfluorobenzene or methoxychlorobenzene group. The preparation of intermediate dimer acids 69-70 and their coupling with amine 21 to yield compounds A-20 and A-21 is outlined in FIG. 18.

Dimer acids 69 and 70. Esters 64 (0.24 g, 0.63 mmol) and 67 (0.52 g, 1.36 mmol) were saponified and the 2-fluoro groups substituted by a methoxy group in one step, using NaOH in MeOH at 60° C. for 16 hr according to Procedure C, giving dimer acids 69 (0.22 g, >95%, $^1$H-NMR) and 70 (0.46 g, 89%, $^1$H-NMR) respectively.

Compounds A-20 and A-21. Coupling of dimer acids 69 and 70 (ca. 100 mg scale) with amine 21 was carried out according to procedure A, providing compounds A-20 and A21, respectively.

EXAMPLE K

Figure 19:
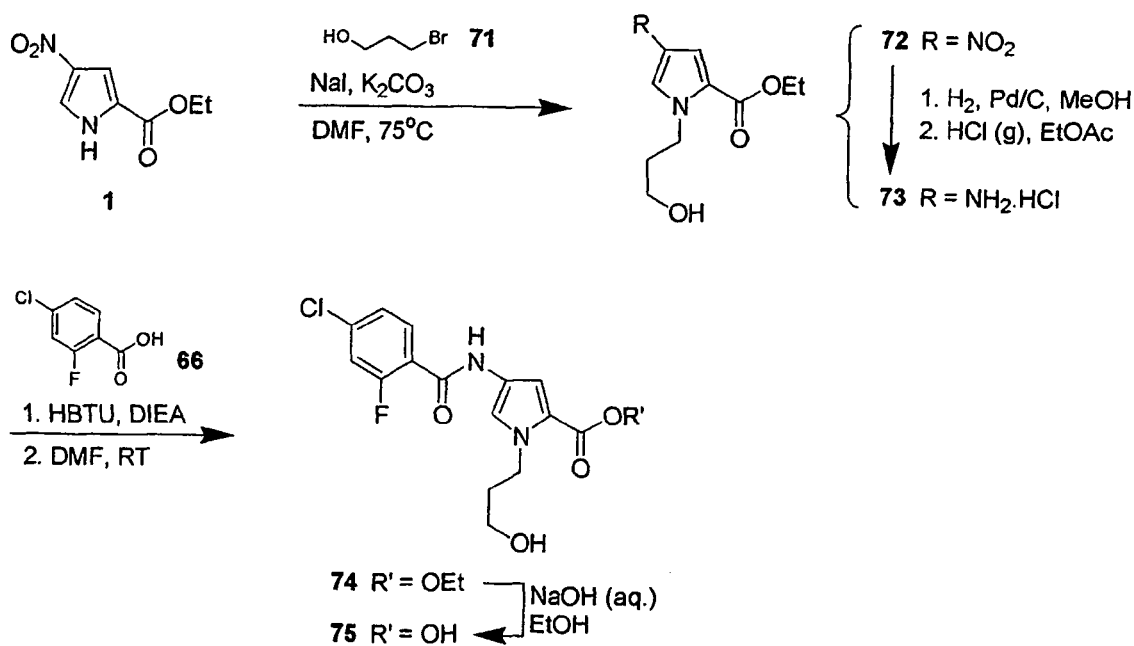
Figure 20:
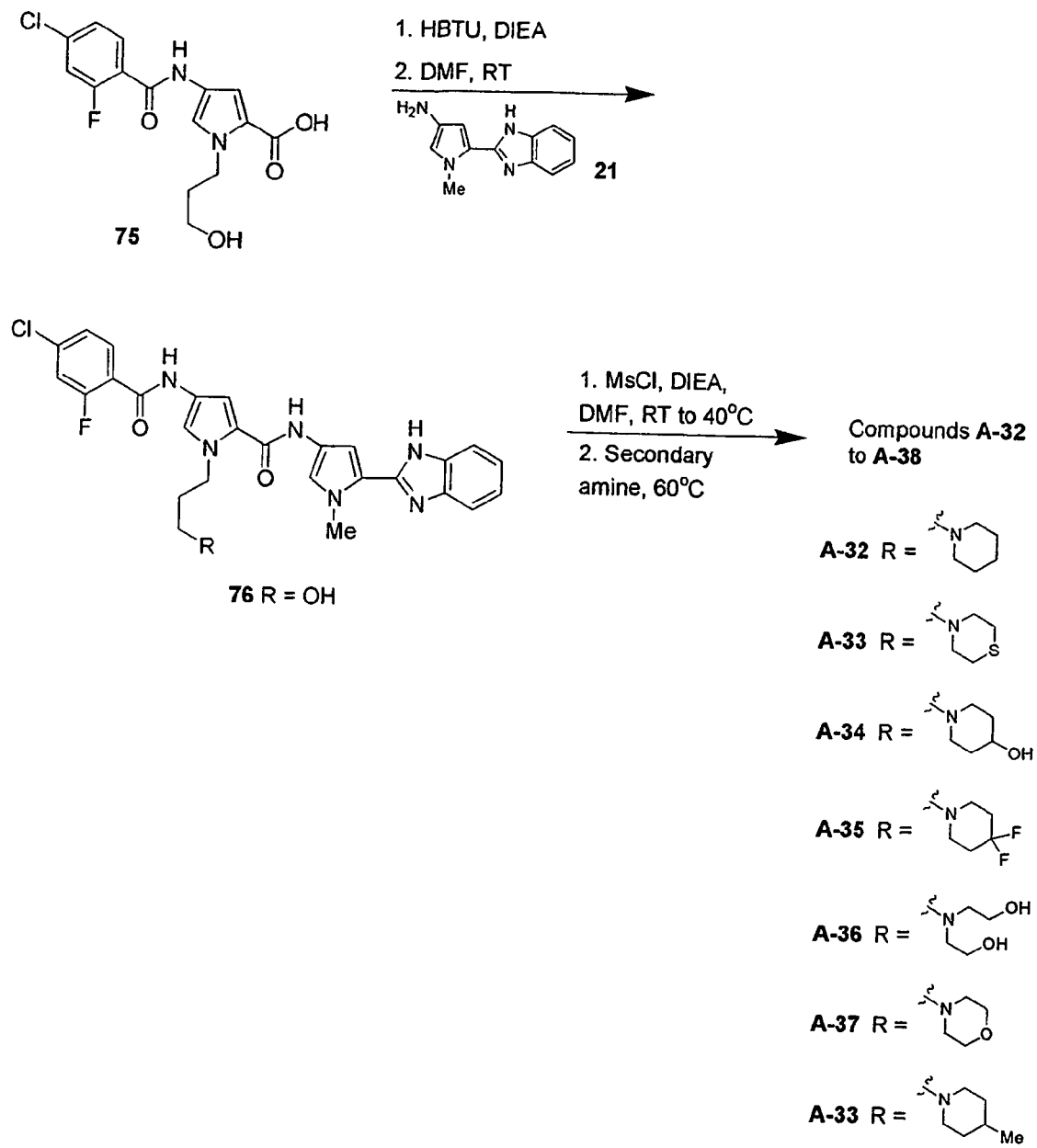

This example describes the synthesis of a subgenus of compounds (I) in which Ar is a chlorofluorobenzene group. The preparation of intermediate dimer acid 75 is shown in FIG. 19. FIG. 20 details the preparation of succeeding intermediate alcohol 76 and its conversion to compounds A-32 to A-38.

Compound 72. A mixture of pyrrole 1 (100 g, 0.54 mmol), 1-bromopropanol 71 (68.5 mL, 1.4 eq.), NaI (40.6 g, 0.5 eq.), and $K_2CO_3$ (150 g, 2 eq.) in DMT (1 L) was stirred at 75° C. for 16 hr. After cooling, the mixture was poured into water (800 mL) and extracted with $Et_2O$ (6×200 mL). The organic layers were dried ($MgSO_4$) and evaporated to give compound 72 (109 g, 83%, $^1$H-NMR) as an orange oil, which was used without further purification.

Amino pyrrole 73. Compound 72 (109 g, 0.45 mol) was reduced according to Procedure B in MeOH. Following removal of solvent, the crude dark brown oil product was taken up in EtOAc (500 mL) and MeOH (50 mL) and cooled in an ice bath. HCl gas was bubbled through the solution for ca. 60 sec. Evaporation of the solvents gave amino pyrrole 73 (103 g, 92% $^1$H-NMR) as an off-white solid.

Dimer ester 74. Amino pyrrole 73 (40 g, 0.16 mol) was coupled to 4-chloro-2-fluorobenzoic acid (66) (28.1 g) according to Procedure A to give dialer ester 74 (46.0 g, 78%, $^1$H-NMR).

Dimer acid 75. Dimer ester 74 (46 g, 0.125 mol) was saponified using NaOH in EtOH at 60° C. for 16 hr according to Procedure C, giving dimer acid 75 (37.4 g, 88%, $^1$H-NMR).

Alcohol 76. Amino pyrrole 21 (30.8 mmol, 1.5 eq.) was coupled to dimer acid 75 (7 g, 20.5 mmol) according to Procedure A to give intermediate alcohol 76 (4.5 g, 41%, $^1$H-NMR).

Compound A-32. Alcohol 76 (100 mg, 0.187 mmol) was mesylated and then heated with piperidine (10 eq.) according to Procedure D to give compound A-32 (25 mg 22%, $^1$H-NMR).

Compounds A-33 to A-38. Compounds A-33 to A-38 were made in analogy to compound A-32 by mesylation of alcohol 76 and subsequent treatment with the corresponding amine according to Procedure D.

EXAMPLE L

Figure 21:
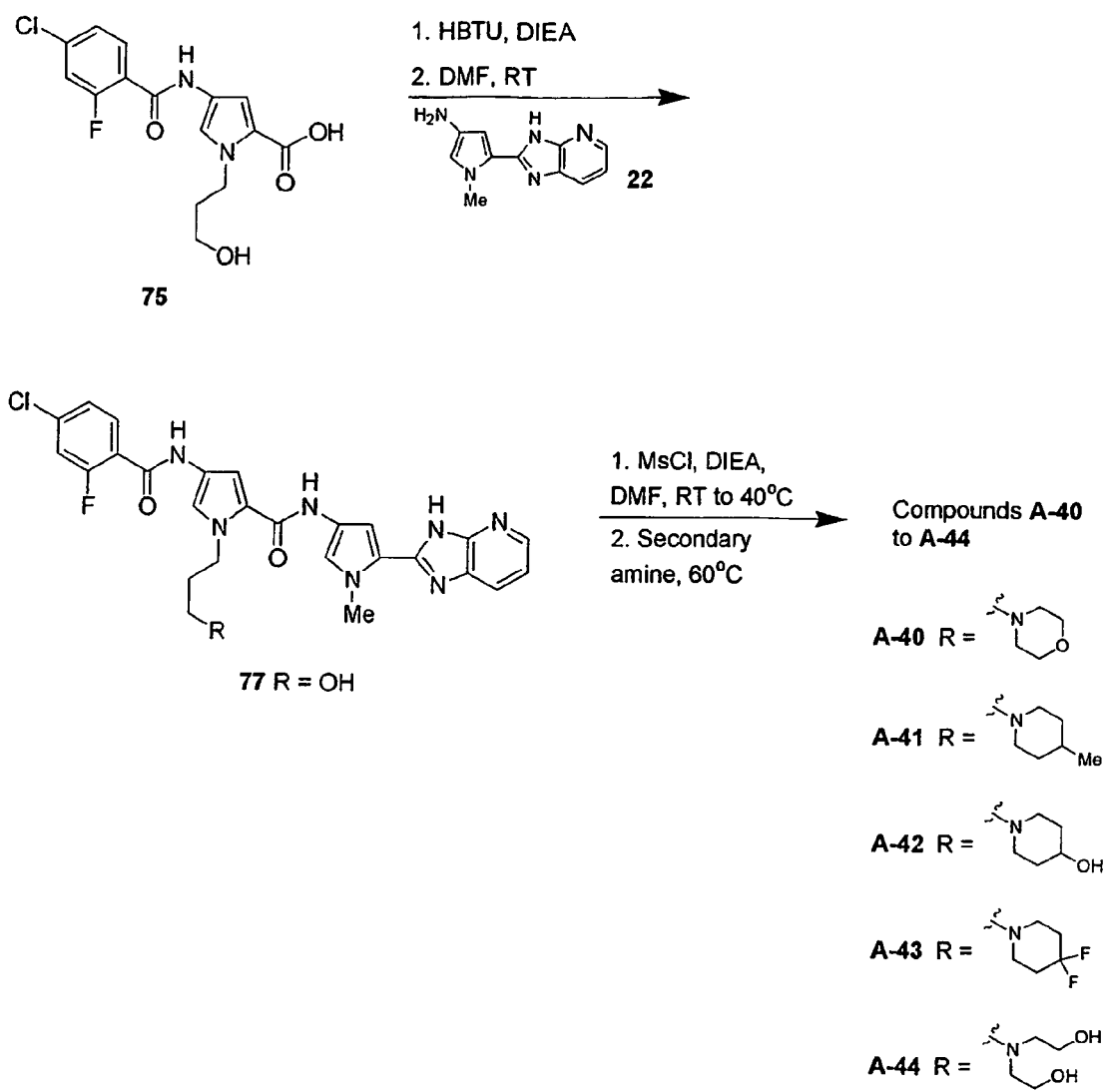

This example describes the synthesis of yet another subgenus of compounds (I) in which Ar is a chlorofluorobenzene groups. FIG. 21 details the preparation of intermediate alcohol 77 and its conversion to compounds A-40 to A-44.

Alcohol 77. Amino pyrrole 22 (3.87 mmol, 1.2 eq.) was coupled to dimer acid 75 (1.1 g, 3.23 mmol) according to procedure A to give alcohol 77 (0.68 g, 39%, $^1$H-NMR).

Compound A-40. Alcohol 77 (88 mg, 0.164 mmol) was mesylated and then heated with morpholine (10 eq.) according to Procedure D to give compound A-40 (19 mg, 20%, $^1$H-NMR).

Compounds A-41 to A-44. These were made in analogy to compound A-40 by mesylation of alcohol 77 and then heating with the corresponding amine.

EXAMPLE M

Figure 22:
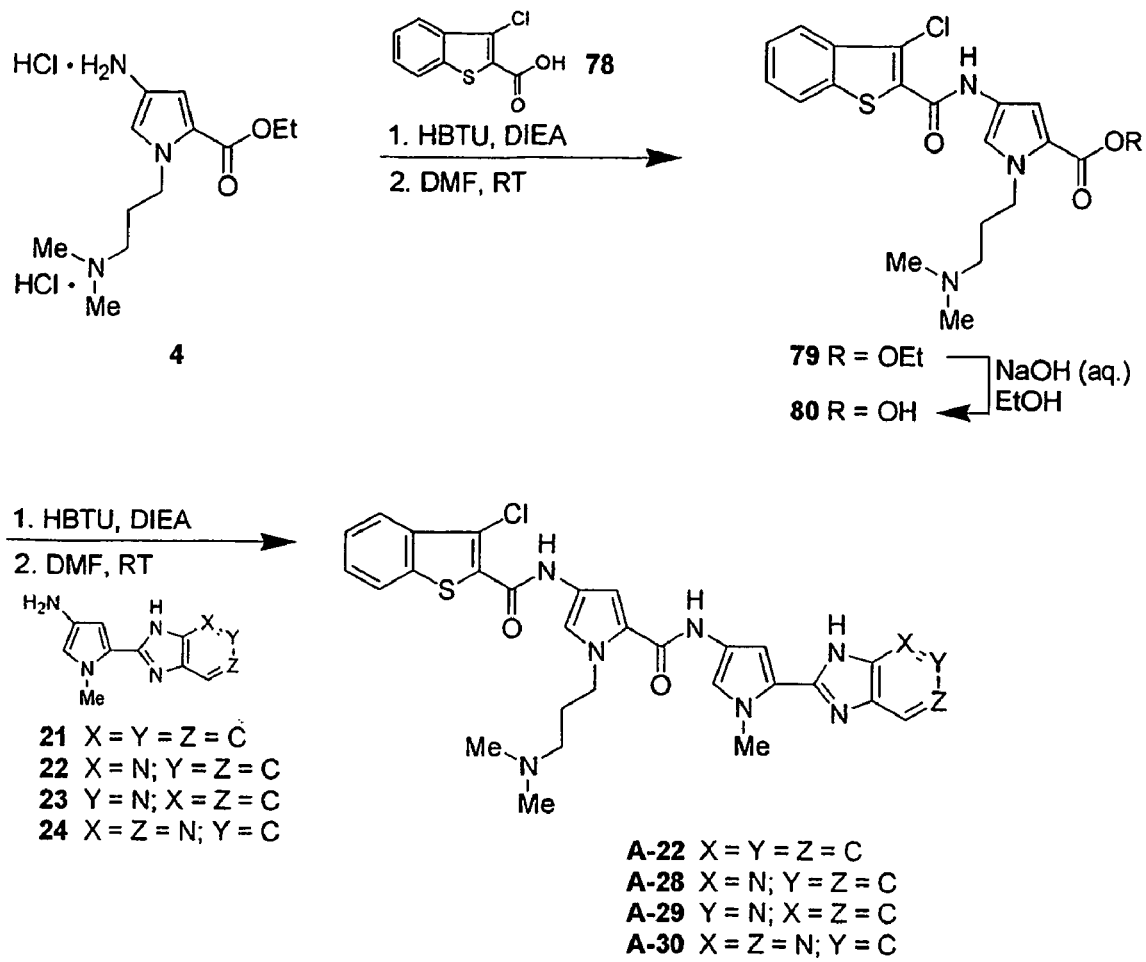

This example describes the synthesis of a subgenus of compounds (I) in which Ar is a 3-chlorobenzothiophene group. The preparation of intermediate dimer acid 80 and its coupling with amines 21-24 in preparation of compounds A-22, A-28, A-29, and A-30 is outlined in FIG. 22.

Dimer ester 79. Amino pyrrole 4 (4.10 g, 13.14 mmol) was coupled to carboxylic acid 78 (3.4 g) according to Procedure A to give dimer ester 79 (536 g, 94%, $^1$H-NMR).

Dimer acid 80. Dimer ester 79 (5.36 g, 12.35 mmol) was saponified using NaOH in EtOH at 60° C. for 16 hr according to Procedure C, giving dimer acid 80 (5.1 g, >95%, $^1$H-NMR).

Compounds A-22 and A-28 to A-30. Coupling of dimer acid 80 (ca. 100 mg scale) with amines 21 to 24 was carried out according to Procedure A, providing compounds A-22 and A-28 to A-30.

EXAMPLE N

Figure 23:
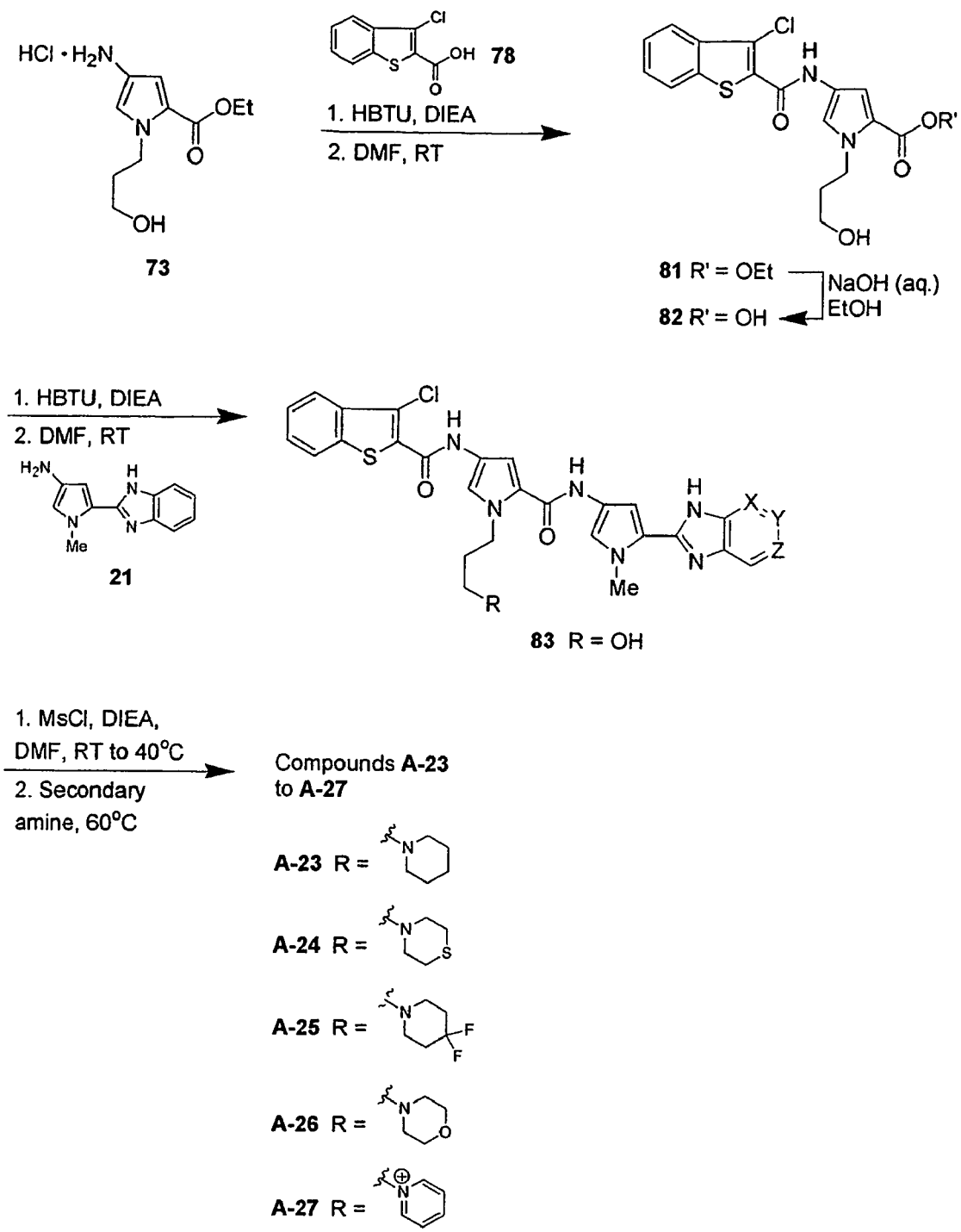

This example describes the synthesis of another subgenus of compounds (I) in which Ar is a 3-chlorobenzothiophene group. 1' he preparation of intermediate dimer acid 82 is shown in FIG. 23, along with its transformation to intermediate alcohol 83 and the latter's conversion to compounds A-23, A-24, A-25, A-26 and A-27.

Dimer ester 81. Amino pyrrole 73 (35 g, 0.14 mol) was coupled to 3-chlorobenzothiophene-2-carboxylic acid 78 (30.1 g) according to Procedure A to give diner ester 81 (48.4 g, 85%, $^1$H-NMR).

Dimer acid 82. Dimer ester 81 (48 g, 0.119 mol) was saponified using NaOH in EtOH at 60° C. for 16 hr according to Procedure C, giving dimer acid 82 (40.6 g, 90%, $^1$H-NMR).

Alcohol 83. Amino pyrrole 21 (31.65 mmol, 1.5 eq.) was coupled to dimer acid 82 (8 g, 21.1 mmol) according to Procedure A to give alcohol 83 (3.02 g, 25%, $^1$H-NMR).

Compound A-26. Alcohol 83 (70 mg, 0.122 mmol) was mesylated and then healed with morpholine (8 eq.) according to Procedure D to give compound A-26 (17 mg, 22%, $^1$H-NMR).

Compounds A-23-A-25 and A-27. These compounds were made analogously to compound A-26 from alcohol 83 and the corresponding amine or pyridine.

EXAMPLE O

Figure 24:
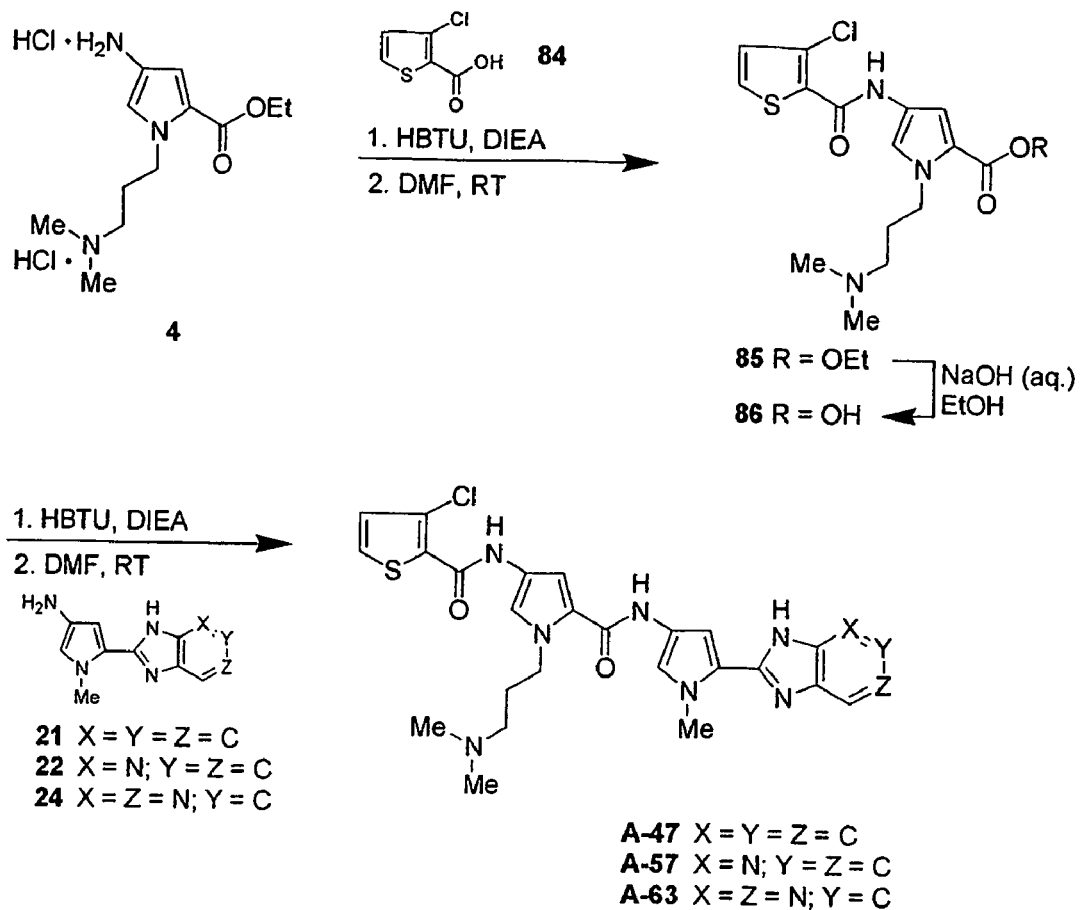

This example describes the synthesis of a subgenus of compounds (I) in which Ar is a 3-chlorothiophene group. The preparation of intermediate dimer acid 86, its coupling with amines 21-22 and 24, and the preparation of compounds A-47, A-57 and A-63 is outlined in FIG. 24.

Dimer ester 85. Pyrrole 4 (2.1 g, 6.73 mmol) was coupled to carboxylic acid 84 (1.31 g) according to Procedure A to give dimer ester 85 (2.12 g, 82%, $^1$H-NMR).

Dimer acid 86. Dimer ester 85 (2.1 g, 5.52 mmol) was saponified using NaOH in EtOH at 60° C. for 12 hr according to Procedure C, giving dimer acid 86 (1.95 g, >95%, $^1$H-NMR).

Compounds A-47, A-57 and A-63. Coupling of dimer acid 86 (ca. 100 mg scale) with amines 21, 22 and 24 was carried out according to Procedure A, providing corresponding compounds A-47, A-57, and A-63.

EXAMPLE P

Figure 25:
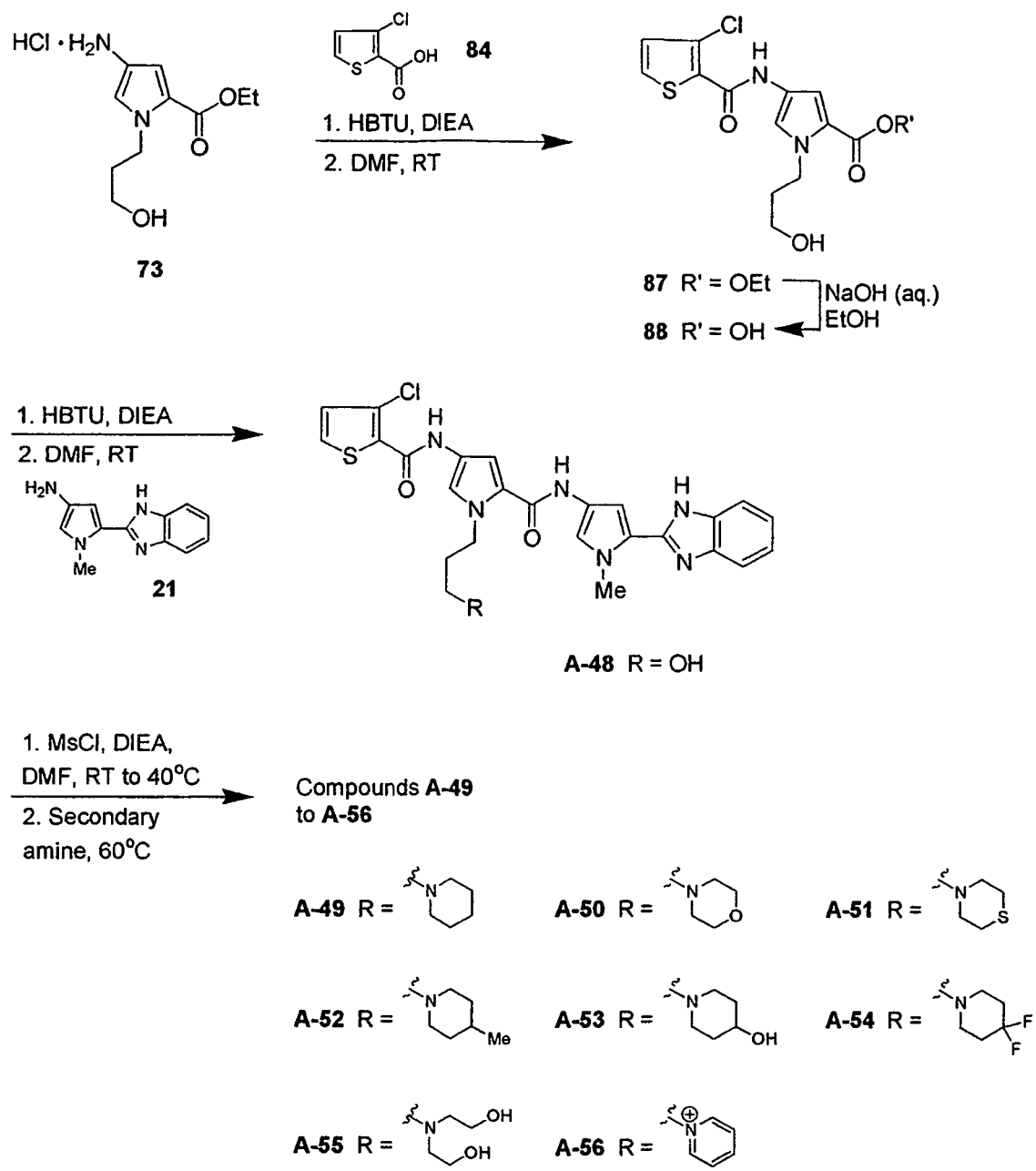

This example describes the synthesis of another subgenus of compounds (I) in which Ar is a 3-chlorothiophene group. FIG. 25 shows the preparation of chlorothiophene-pyrrole dimer acid 88, its transformation to compound A-48, and the latter's conversion to compounds A-49 to A-56.

Dimer ester 87. Pyrrole 73 (40 g, 0.16 mol) was coupled to carboxylic acid 84 (26.2 g) according to Procedure A to give dimer ester 87 (44.5 g, 78%, $^1$H-NMR).

Dimer acid 88. Dimer ester 87 (35.6 g, 0.10 mmol) was saponified using KOH in EtOH at 60° C. for 6 hr according to Procedure C, giving timer acid 88 (32.5 g, >95%, $^1$H-NMR).

Compound A-48. Amine 21 (17.3 mmol, 1 eq.) was coupled to dimer acid 88 (5.68 g, 17.3 mmol) according to Procedure A to give compound A-48 (3.01 g, 34%, $^1$H-NMR).

Compound A-51. Compound A-48 (64 mg, 0.122 mmol) was mesylated and then healed with thiomorpholine (9 eq.) according to Procedure D to give compound A-51 (25 mg, 34%, $^1$H-NMR).

Compounds A-49 to A-50 and A-52 to A-56. These compounds were made analogously to compound A-51 by the mesylation of alcohol A-48 and then healing with the corresponding amine or pyridine.

EXAMPLE Q

Figure 26:
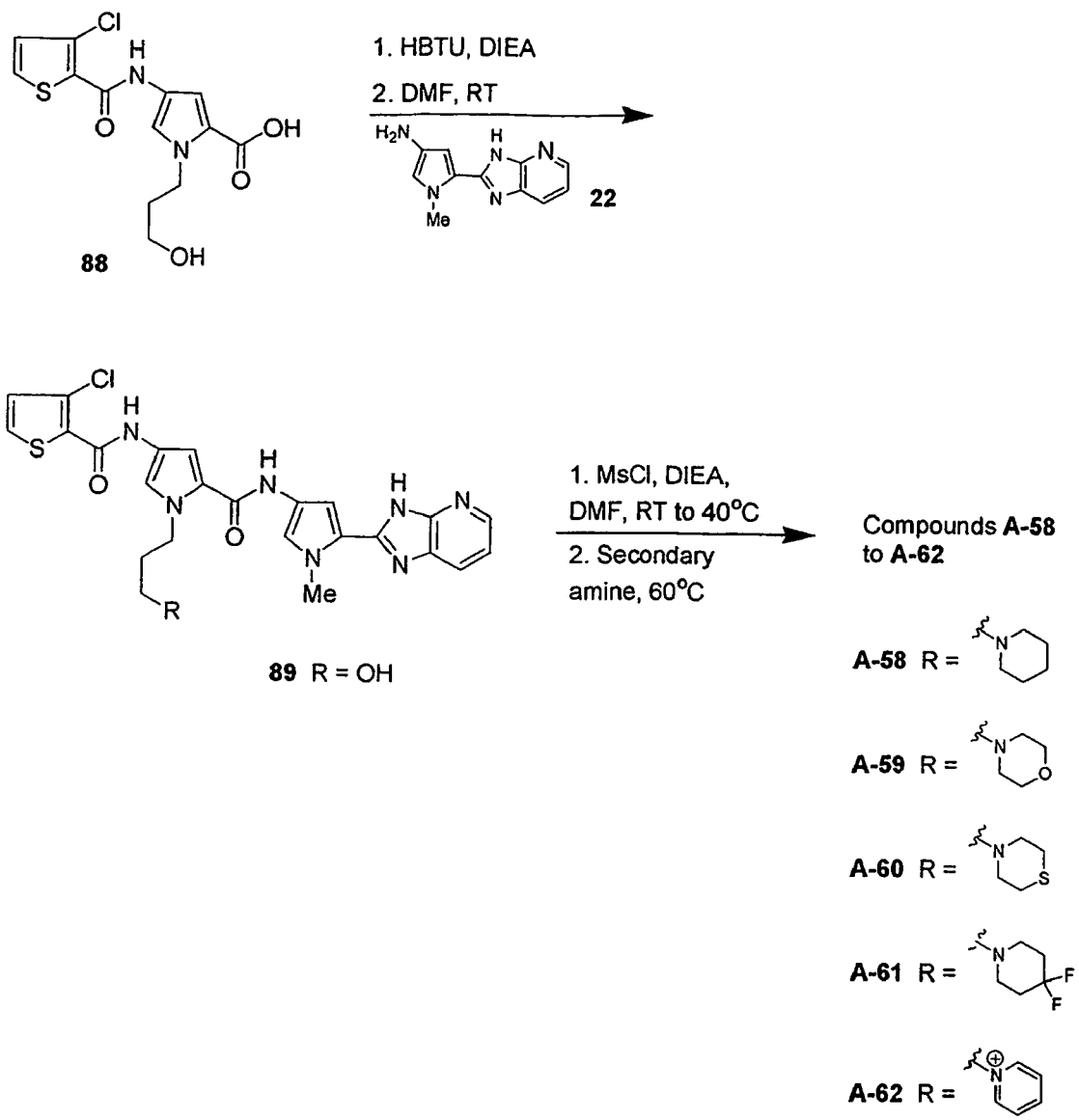

This example describes the synthesis of yet another subgenus of compounds (I) in which Ar is a 3-chlorothiophene group. FIG. 26 details the preparation of intermediate alcohol 89 and its conversion to compounds A-58 to A-62.

Alcohol 89. Amino pyrrole 22 (17.84 mmol, 1 eq.) was coupled to acid 88 (5.87 g, 17.84 mmol) according to Procedure A to give alcohol 89 (2.71 g, 29%, $^1$H-NMR).

Compound A-59. Alcohol 89 (50 mg, 0.095 mmol) was mesylated and then floated with morpholine (10 eq.) according to Procedure D to give compound A-59 (15 mg, 27°/, $^1$H-NMR).

Compounds A-58 and A-60 to A-62. These compounds were made analogously to compound A-59 from alcohol 89 and the corresponding amine or pyridine.

Biological Activity

It vitro biological activity data were collected for a variety of microorganisms, including *Bacillus cereus* (ATCC 11778), *Staphylococcus aureus* (ATCC 33591; ATCC 27660, a methicillin resistant strain (MRSA); ATCC 13709, a methicillin sensitive strain (MSSA)), *Enterococcus faecalis* (ATCC 29212), and *Streptococcus pneumoniae* (ATCC 49619). Additionally, antifungal activity data were collected for *Candida albicans* (ATCC 38247).

Compounds according to this invention were screened for their in vitro activities against selected species of bacteria and fungi. The minimal inhibition concentration (MIC) of these compounds was determined using the National Committee for Clinical Laboratory Standards (NCCLS) broth microdilution assay in microtiter plates, as set forth in: (1) the guidelines of the National Committee for Clinical Laboratory Standards (NCCLS) Document M7-A4 (NCCLS, 1997); (2) the guidelines of the National Committee for Clinical Laboratory Standards (NCCLS) Document M11-A4 (NCCLS, 1997); and (3) the guidelines and reference method of the National Committee for Clinical Laboratory Standards (NCCLS) Document M27-T (NCCLS, 1995). For antifungal assays, the method recommended in Murray, P R., 1995 Manual of Clinical Microbiology (ASM Press, Washington, D.C.), was employed.

The results are presented in Table B below, which is keyed as follows:

Organism Tested Against:

A = *B. cereus* ATCC 11778
B = *C. albicans* ATCC 38247
C = *E. faecalis* ATCC 29212
D = *S. aureus* ATCC 13709
E = *S. aureus* ATCC 27660
F = *S. aureus* ATCC 33591
G = *S. pneumoniae* ATCC 49619

Activity:

+++ = MIC ≤ 4 µg/mL
++ = 4 < MIC < 12 µg/mL
+ = 12 ≤ MIC ≤ 32 µg/mL
ND = not determined
>32 = preliminary data indicates MIC greater than 32 µg/mL

TABLE B

Biological Activity

| Ref. No. | Organism (Minimum Inhibitory Concentration (MIC), µg/mL) | | | | | | |
|---|---|---|---|---|---|---|---|
| | A | B | C | D | E | F | G |
| A-1 | +++ | +++ | +++ | +++ | +++ | +++ | +++ |
| A-2 | +++ | >32 | +++ | +++ | +++ | +++ | +++ |
| A-3 | >32 | >32 | >32 | >32 | >32 | >32 | >32 |
| A-4 | +++ | >32 | +++ | +++ | +++ | +++ | +++ |
| A-5 | +++ | >32 | +++ | +++ | +++ | +++ | +++ |
| A-6 | +++ | >32 | +++ | +++ | +++ | +++ | +++ |
| A-7 | +++ | >32 | +++ | +++ | +++ | +++ | +++ |
| A-8 | ++ | >32 | +++ | +++ | +++ | +++ | +++ |
| A-9 | +++ | >32 | +++ | +++ | +++ | +++ | +++ |
| A-10 | +++ | >32 | +++ | +++ | +++ | +++ | +++ |
| A-11 | +++ | >32 | +++ | +++ | +++ | +++ | +++ |
| A-12 | +++ | >32 | +++ | +++ | +++ | +++ | +++ |
| A-13 | +++ | >32 | +++ | +++ | +++ | +++ | +++ |
| A-14 | +++ | >32 | +++ | +++ | +++ | +++ | +++ |
| A-15 | + | >32 | ++ | + | + | + | +++ |
| A-16 | +++ | + | +++ | +++ | +++ | +++ | +++ |
| A-17 | +++ | >32 | +++ | +++ | +++ | +++ | +++ |
| A-18 | + | >32 | +++ | + | +++ | +++ | +++ |
| A-19 | + | >32 | ++ | + | + | + | +++ |
| A-20 | +++ | + | +++ | +++ | +++ | ND | +++ |
| A-21 | +++ | + | +++ | ++ | +++ | ND | +++ |
| A-22 | +++ | + | ++ | ++ | ++ | ND | ++ |
| A-23 | +++ | + | +++ | +++ | +++ | +++ | +++ |
| A-24 | >32 | >32 | +++ | +++ | +++ | +++ | +++ |
| A-25 | >32 | >32 | + | + | + | + | ++ |
| A-26 | +++ | >32 | +++ | +++ | +++ | +++ | +++ |
| A-27 | + | + | + | ++ | ++ | ++ | + |
| A-28 | +++ | >32 | +++ | +++ | +++ | +++ | +++ |
| A-29 | +++ | ++ | +++ | +++ | +++ | +++ | +++ |
| A-30 | +++ | ++ | +++ | +++ | +++ | +++ | +++ |
| A-31 | +++ | + | +++ | +++ | +++ | +++ | +++ |
| A-32 | +++ | + | +++ | +++ | +++ | +++ | +++ |
| A-33 | +++ | >32 | +++ | +++ | +++ | +++ | +++ |
| A-34 | +++ | + | +++ | +++ | +++ | +++ | +++ |
| A-35 | +++ | >32 | +++ | +++ | +++ | +++ | +++ |
| A-36 | ++ | + | +++ | ++ | +++ | +++ | +++ |
| A-37 | +++ | >32 | +++ | +++ | +++ | +++ | +++ |
| A-38 | +++ | + | +++ | +++ | +++ | +++ | +++ |
| A-39 | +++ | + | +++ | +++ | +++ | +++ | +++ |
| A-40 | +++ | >32 | +++ | +++ | +++ | +++ | +++ |
| A-41 | +++ | >32 | +++ | +++ | +++ | +++ | +++ |
| A-42 | +++ | + | +++ | +++ | +++ | +++ | +++ |
| A-43 | +++ | >32 | ++ | ++ | +++ | ++ | +++ |
| A-44 | + | >32 | ++ | ++ | +++ | +++ | +++ |
| A-45 | +++ | ++ | +++ | +++ | +++ | +++ | +++ |
| A-46 | +++ | >32 | +++ | +++ | +++ | +++ | +++ |
| A-47 | +++ | + | +++ | +++ | +++ | +++ | +++ |
| A-48 | +++ | >32 | +++ | +++ | +++ | +++ | +++ |
| A-49 | +++ | + | +++ | +++ | +++ | +++ | +++ |
| A-50 | +++ | >32 | +++ | +++ | +++ | +++ | +++ |
| A-51 | +++ | >32 | +++ | +++ | +++ | +++ | +++ |
| A-52 | +++ | + | +++ | +++ | +++ | +++ | +++ |
| A-53 | +++ | + | ++ | +++ | +++ | +++ | +++ |
| A-54 | +++ | >32 | +++ | +++ | +++ | +++ | +++ |
| A-55 | + | >32 | + | + | ++ | ++ | ++ |
| A-56 | >32 | >32 | >32 | + | + | + | >32 |
| A-57 | ++ | >32 | +++ | +++ | +++ | +++ | +++ |
| A-58 | +++ | >32 | +++ | +++ | +++ | +++ | +++ |
| A-59 | +++ | >32 | +++ | +++ | +++ | +++ | +++ |
| A-60 | +++ | >32 | +++ | +++ | +++ | +++ | +++ |
| A-61 | +++ | >32 | +++ | +++ | +++ | +++ | +++ |
| A-62 | >32 | >32 | >32 | >32 | + | + | + |
| A-63 | >32 | >32 | + | + | + | + | +++ |

Additionally, some compounds were screened against *Enterococcus faccium* (ATCC 51559, a vancomycin resistant strain (VRE)), *Staphylococcus epidermidis* (ATCC 12228), *Streptococcus pneumoniae* (ATCC 51422, a penicillin resistant strain (PRSP)), and/or *Streptococcus pyogenes* (ATCC 49399). These results are provided in Table C, keyed as follows:

Organism Tested Against:

A = *E. faecium* ATCC 51559  B = *S. epidermidis* ATCC 12228
C = *S. pneumoniae* ATCC 51422  D = *S. pyogenes* ATCC 4399

Activity:

+++ = MIC ≤ 4 pg/mL  ++ = 4 < MIC < 12 µg/mL
+ = 12 ≤ MIC ≤ 32 µg/mL  ND = not determined
>32 = preliminary data indicates MIC greater than 32 µg/ml,

TABLE C

Additional Biological Data

| Ref. No. | Organism (Minimum Inhibitory Concentration (MIC), µg/mL) | | | | | | |
|---|---|---|---|---|---|---|---|
| | A | B | C | D | E | F | G |
| A-1 | +++ | +++ | +++ | +++ | +++ | +++ | +++ |
| A-2 | +++ | +++ | +++ | +++ | +++ | +++ | +++ |
| A-4 | +++ | +++ | +++ | +++ | +++ | +++ | +++ |
| A-5 | +++ | +++ | +++ | +++ | +++ | +++ | +++ |
| A-7 | +++ | +++ | +++ | +++ | +++ | +++ | +++ |
| A-16 | +++ | +++ | +++ | +++ | +++ | +++ | ND |
| A-43 | +++ | +++ | ++ | ++ | +++ | ++ | +++ |
| A-45 | +++ | +++ | +++ | +++ | +++ | +++ | +++ |
| A-48 | +++ | +++ | +++ | +++ | +++ | +++ | +++ |
| A-49 | +++ | +++ | +++ | +++ | +++ | +++ | +++ |
| A-50 | +++ | +++ | +++ | +++ | +++ | +++ | +++ |
| A-51 | +++ | +++ | +++ | +++ | +++ | +++ | +++ |
| A-54 | +++ | +++ | +++ | +++ | +++ | +++ | +++ |

Preferably, compounds of this invention have an MIC of 4 or less against at least one strain of drug resistant bacteria, such as *Staphylococcus aereus* (ATCC 27660), *Streptococcus pneumoniae* (ATCC 51422), and *Enterococcus faecium* (ATCC 51559).

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

What is claimed is:

1. A compound according to formula (I)

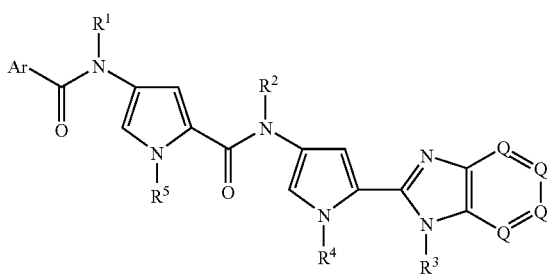

or a solvate, prodrug or a pharmaceutically acceptable salt thereof, wherein

Ar is an unsubstituted or substituted phenyl group, 5-member heteroaryl group, 6-member heteroaryl group, 6,6-condensed ring aryl or heteroaryl group, or 6,5-condensed ring heteroaryl group;

each Q is independently N, CH, C($R^6$), where $R^6$ is as defined hereinbelow, with the proviso that no more than two Q's are N;

each of $R^1$, $R^2$, $R^3$, and $R^4$ independently is H or a ($C_1$-$C_5$) alkyl group;

each $R^5$ is independently H, a substituted or unsubstituted ($C_1$-$C_{12}$)alkyl group, or a substituted or unsubstituted ($C_1$-$C_{12}$) heteroalkyl group; and each $R^6$ is independently a substituted or unsubstituted ($C_1$-$C_{12}$) alkyl, $OR^5$, $N(R^5)_2$, $O(CO)R^5$, $N(CO)R^5$, Cl, F, or Br.

2. A compound according to claim 1, represented by the formula (II)

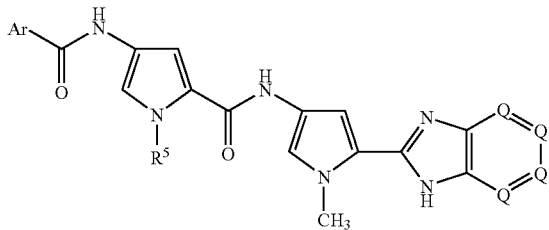

3. A compound according to claim 1, wherein Ar is an unsubstituted or substituted phenyl, imidazolyl, pyrrolyl, pyrazolyl, furanyl, isothiazolyl, oxazolyl, isoxazolyl, thiazolyl, furazanyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,3,4-oxadiazolyl, 1,2,4-oxadiazolyl, thienyl, pyridyl, pyrimidyl, pyrazinyl, pyridazinyl, triazinyl, naphthyl, quinolyl, isoquinolyl, benzothienyl, indolyl, or benzofuranyl group.

4. A compound according to claim 1, wherein Ar is selected from the group consisting of

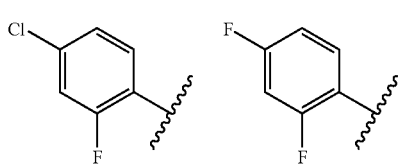

-continued

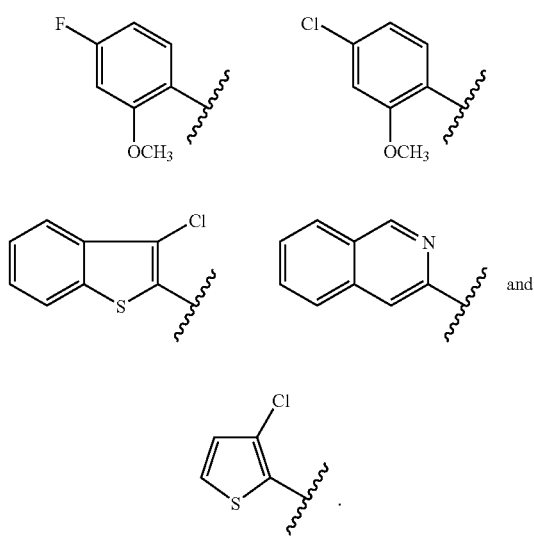

5. A compound according to claim 1, wherein the 6,5-condensed ring system

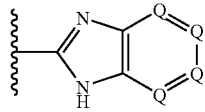

is selected from the group consisting of

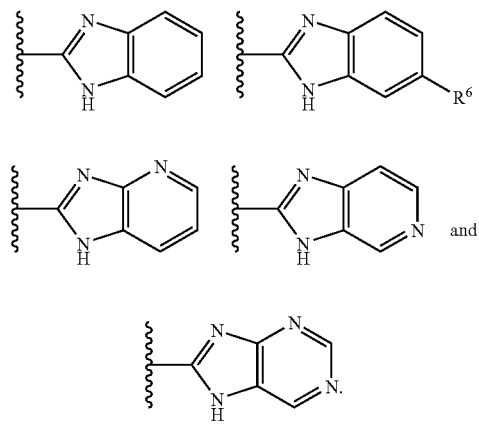

6. A compound according to claim 1, wherein in the 6,5-condensed ring system

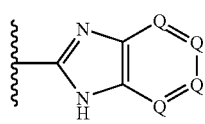

at least one Q is N.

7. A compound according to claim 1, represented by the formula (III):

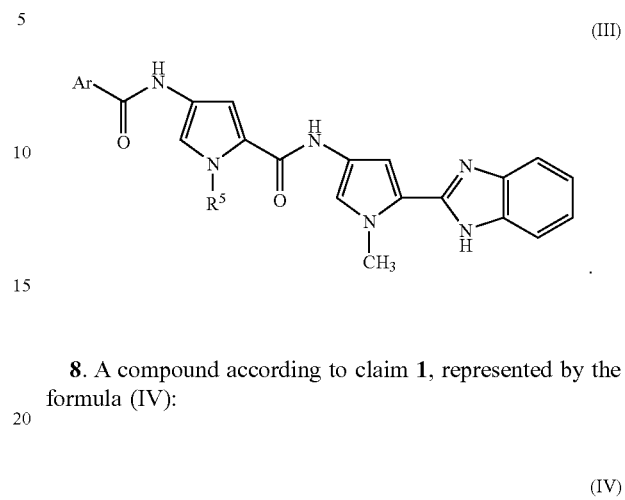

8. A compound according to claim 1, represented by the formula (IV):

(IV)

9. A compound according to claim 1, represented by the formula (V):

(V)

10. A compound according to claim 1, represented by the formula (VI):

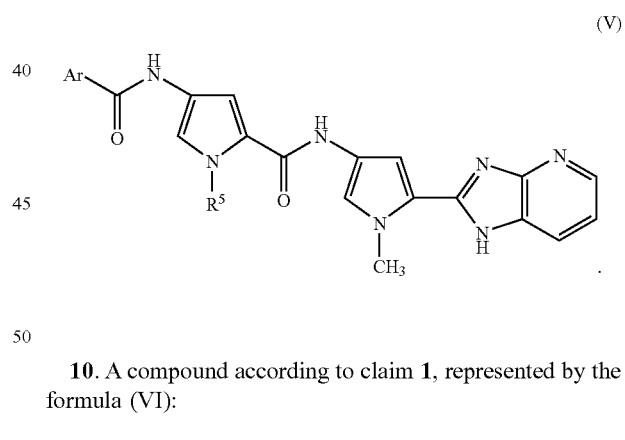

11. A compound according to claim 1, represented by the formula (VII):

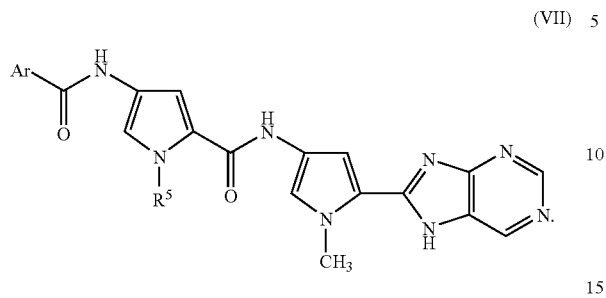
(VII)

12. A compound according to claim 1, wherein each of $R^1$, $R^2$, and $R^3$ is H.

13. A compound according to claim 1, wherein $R^4$ is methyl.

14. A compound according to claim 1, wherein $R^5$ is methyl, ethyl, propyl, isopropyl, $(CH_2)n(Am)$, or $(CH_2)n(OH)$, where n is 2, 3, 4, or 5 and Am is an alkyl amine group or a quaternary ammonium group.

15. A compound according to claim 14, wherein $R^5$ is $(CH_2)_3(Am)$.

16. A compound according to claim 14, wherein $R^5$ is selected from the group consisting of

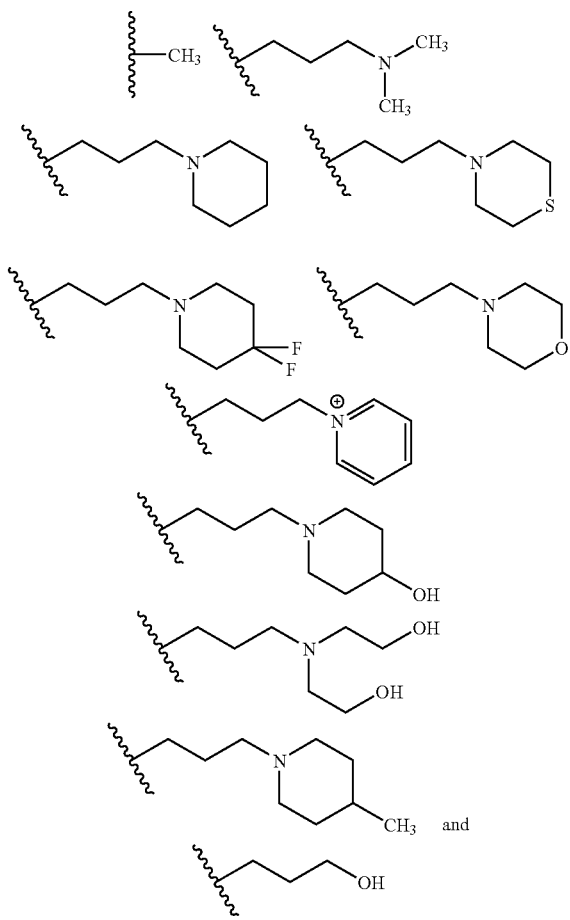

17. A compound according to claim 1, wherein $R^5$ is methyl, Ar is

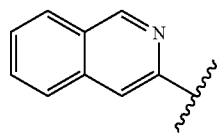

and in the condensed 6,5 ring system

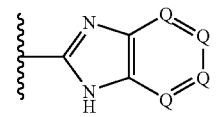

at least one Q is N and the remaining Q's are CH.

18. A compound according to claim 1, wherein Ar is selected from the group consisting of

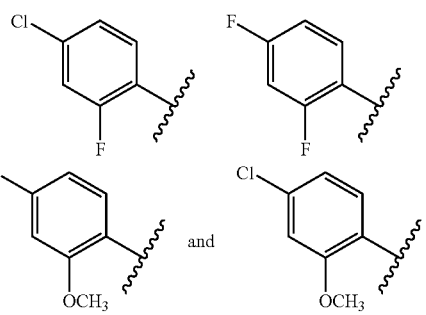

and $R^5$ is $(CH_2)_3N(CH_3)_2$.

19. A compound according to claim 1, wherein $R^6$ is methyl, ethyl, propyl, isopropyl, $OR^5$, $NH(CO)R^5$, $O(CO)R^5$, $N(R^5)$, or Cl.

20. A compound according to claim 1, wherein $R^6$ is selected from the group consisting of:

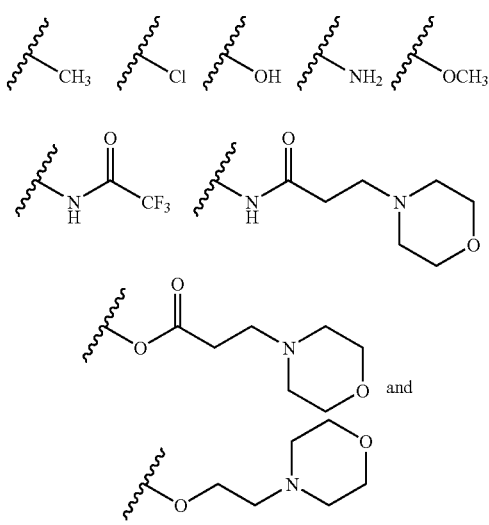

21. A compound according to claim 1, having a minimum inhibitory concentration of 4 µg/mL or less against at least one of *Staphylococcus aureus* (ATCC 27660), *Streptococcus pneumoniae* (ATCC 51422), and *Enterococcus faecium* (ATCC 51559).

22. A method of treating a bacterial infection in a mammal, comprising administering to a patient in need of such treatment an effective amount of a compound according to claim 1.

23. A method according to claim 22, wherein the bacterial infection is an infection by drug resistant bacteria.

24. A method according to claim 23, wherein the drug resistant bacteria is MRSA, PRSP, or VRE.

* * * * *